(12) United States Patent
Liu et al.

(10) Patent No.: US 10,709,351 B2
(45) Date of Patent: Jul. 14, 2020

(54) MAGNETIC RESONANCE IMAGING APPARATUS, MAGNETIC RESONANCE IMAGING METHOD AND MAGNETIC RESONANCE IMAGING SYSTEM

(71) Applicant: Canon Medical Systems Corporation, Otawara-shi (JP)

(72) Inventors: Ye Liu, Chaoyang Beijing (CN); Bin Fu, Chaoyang Beijing (CN); Bing Li, Chaoyang Beijing (CN); Jinbiao Zhang, Chaoyang Beijing (CN); Xiaofei Sun, Chaoyang Beijing (CN); Kensuke Shinoda, Otawara (JP); Satoshi Sugiura, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 82 days.

(21) Appl. No.: 15/934,417

(22) Filed: Mar. 23, 2018

(65) Prior Publication Data
US 2018/0271399 A1    Sep. 27, 2018

Related U.S. Application Data

(63) Continuation-in-part of application No. 15/823,905, filed on Nov. 28, 2017.

(30) Foreign Application Priority Data

Mar. 24, 2017  (CN) .......................... 2017 1 0182311
Nov. 6, 2017   (JP) ................................ 2017-213700
Mar. 9, 2018   (JP) ................................ 2018-043424

(51) Int. Cl.
*G01R 33/20*   (2006.01)
*A61B 5/00*    (2006.01)
(Continued)

(52) U.S. Cl.
CPC .............. *A61B 5/055* (2013.01); *A61B 5/743* (2013.01); *A61B 5/748* (2013.01); *A61B 5/7435* (2013.01);
(Continued)

(58) Field of Classification Search
CPC .... G01R 33/20; G01R 33/5608; G06T 15/08; G06T 19/20
(Continued)

(56) References Cited

U.S. PATENT DOCUMENTS

| | | | |
|---|---|---|---|
| 8,467,588 B2* | 6/2013 | Long ..................... | G06T 7/149 382/110 |
| 2011/0235883 A1* | 9/2011 | Nakagawa .............. | G06T 7/12 382/131 |

(Continued)

FOREIGN PATENT DOCUMENTS

| CN | 102908142 | 2/2013 |
|---|---|---|
| CN | 104102013 A | 10/2014 |

OTHER PUBLICATIONS

Office Action dated Jul. 25, 2019 in related U.S. Appl. No. 15/823,905.

*Primary Examiner* — Dwayne D Bost
*Assistant Examiner* — Stephen M Brinich
(74) *Attorney, Agent, or Firm* — Oblon, McClelland, Maier & Neustadt, L.L.P.

(57) ABSTRACT

A magnetic resonance imaging apparatus according to an embodiment includes a display, an input interface, and processing circuitry. The display displays at least a locator image and a reference image. The input interface sets a region of interest on the locator image displayed on the display. The processing circuitry scans a subject to obtain three dimensional data, generates a locator image from the three dimensional data and displaying the locator image on the display, generates a reference image corresponding to the
(Continued)

location of the region of interest and displaying the reference image on the display, and makes, when a size or position of the region of interest on one of the locator image and the reference image is changed by the input interface, adjustments to correspondingly change the display magnification or position of the other one of the locator image and the reference image.

14 Claims, 14 Drawing Sheets

(51) Int. Cl.
*A61B 5/055* (2006.01)
*G01R 33/54* (2006.01)
*G01R 33/483* (2006.01)

(52) U.S. Cl.
CPC ............ *G01R 33/20* (2013.01); *G01R 33/546* (2013.01); *A61B 5/7425* (2013.01); *G01R 33/4833* (2013.01)

(58) Field of Classification Search
USPC ....... 382/254, 256, 294, 144, 151, 260–261, 382/275, 298–300
See application file for complete search history.

(56) References Cited

U.S. PATENT DOCUMENTS

| | | |
|---|---|---|
| 2012/0081357 A1 | 4/2012 | Habbecke et al. |
| 2012/0249549 A1 | 10/2012 | Endo et al. |
| 2013/0322723 A1 | 12/2013 | Akhbardeh et al. |
| 2013/0328869 A1 | 12/2013 | Choi et al. |
| 2014/0306954 A1 | 10/2014 | Kao |

* cited by examiner

FIG.10
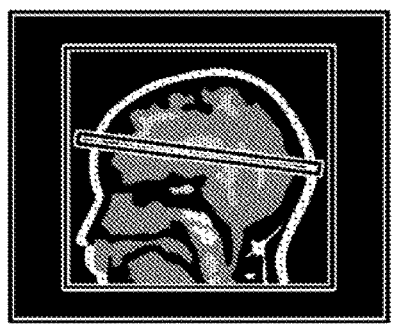
(a)
(b)
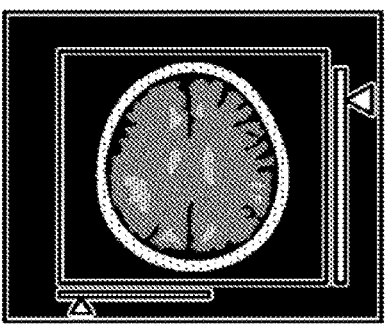
(c)
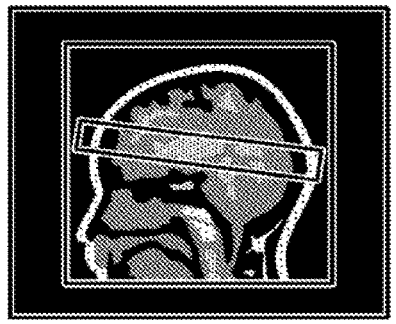
(d)
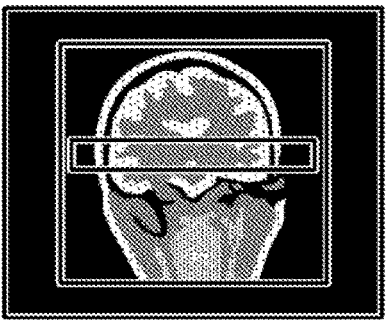
(e)
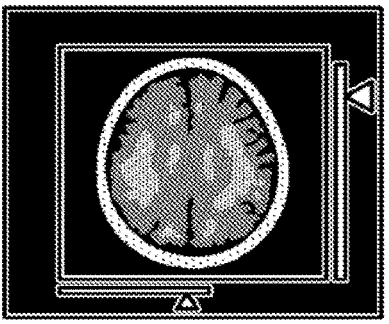
(f)

FIG.11
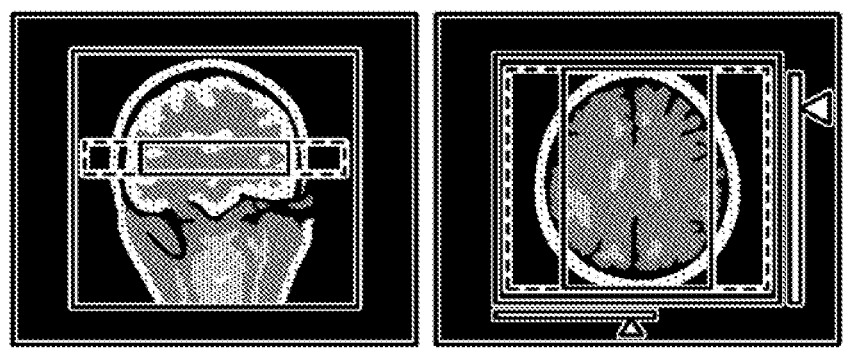
(a)　　　　　　　　(b)
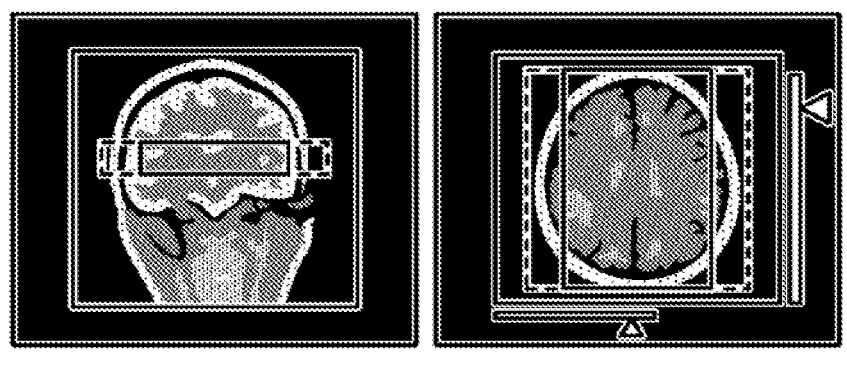
(c)　　　　　　　　(d)

FIG.12
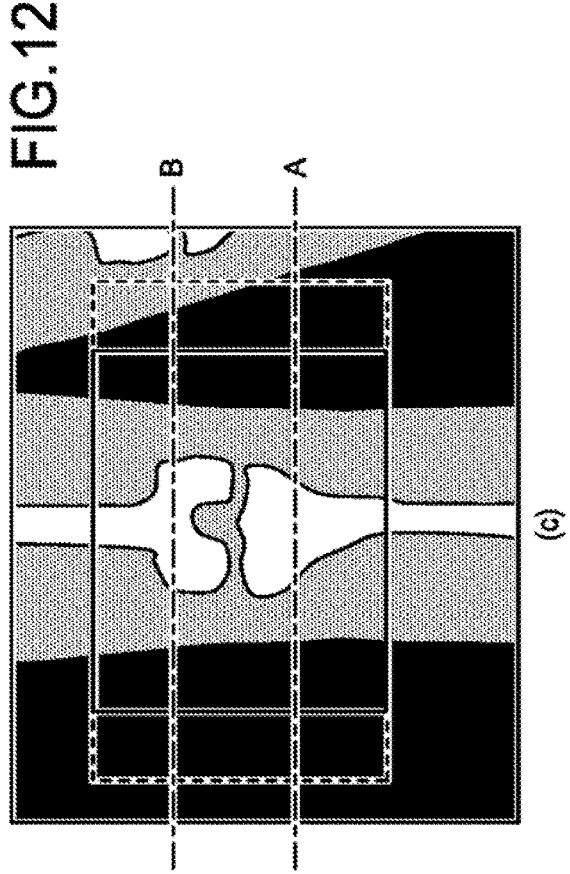
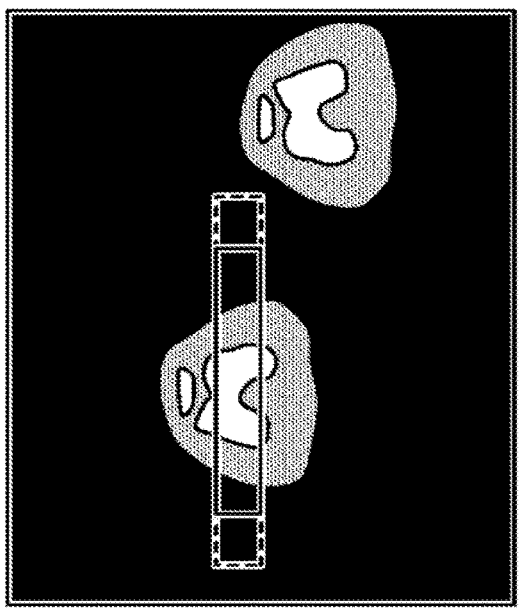
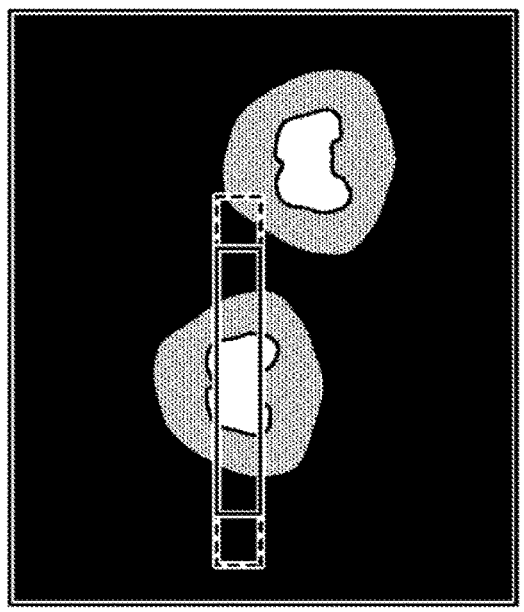

SCAN AREA>OUTLINE OF HEAD

SCAN AREA<OUTLINE OF HEAD

FIG.14
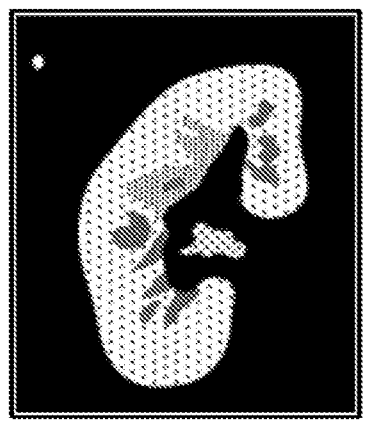
NON-LOCAL EXCITATION SCAN
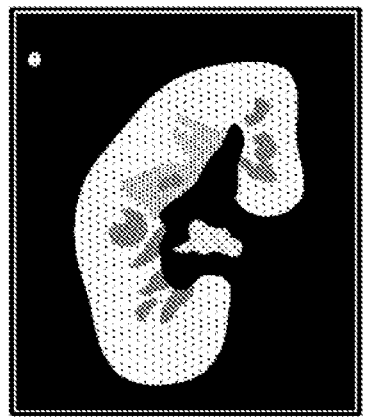
LOCAL EXCITATION SCAN

MAGNETIC RESONANCE IMAGING APPARATUS, MAGNETIC RESONANCE IMAGING METHOD AND MAGNETIC RESONANCE IMAGING SYSTEM

CROSS-REFERENCE TO RELATED APPLICATIONS

This application is a continuation-in-part (CIP) of application Ser. No. 15/823,905 filed on Nov. 28, 2017, the entire contents of which are incorporated herein by reference in this application. This application is also based upon and claims the benefit of priority from Chinese Patent Application No. 201710182311.8, filed on Mar. 24, 2017; Japanese Patent Application No. 2017-213700, filed on Nov. 6, 2017; and Japanese Patent Application No. 2018-043424, filed on Mar. 9, 2018, the entire contents of which are incorporated herein by reference.

FIELD

Embodiments described herein relate to a magnetic resonance imaging apparatus, a magnetic resonance imaging method and a magnetic resonance imaging system.

BACKGROUND

Currently, in magnetic resonance imaging, a graphical slice locator is widely used. The graphical slice locator is a graphical interface based on a reference image, which can visualize and define graphical objects of slice sets of magnetic resonance scan etc.

BRIEF DESCRIPTION OF THE DRAWINGS

FIG. 10 is a schematic view of an example display of a magnetic resonance imaging apparatus according to a fourth embodiment.

FIG. 11 is a schematic view of an example display of a magnetic resonance imaging apparatus according to a fifth embodiment.

FIG. 12 is a schematic view of another example display of the magnetic resonance imaging apparatus according to the fifth embodiment.

FIG. 14 is a schematic view of the image obtained by applying the local excitation scan and the non-local excitation scan.

DETAILED DESCRIPTION

Figure 1:
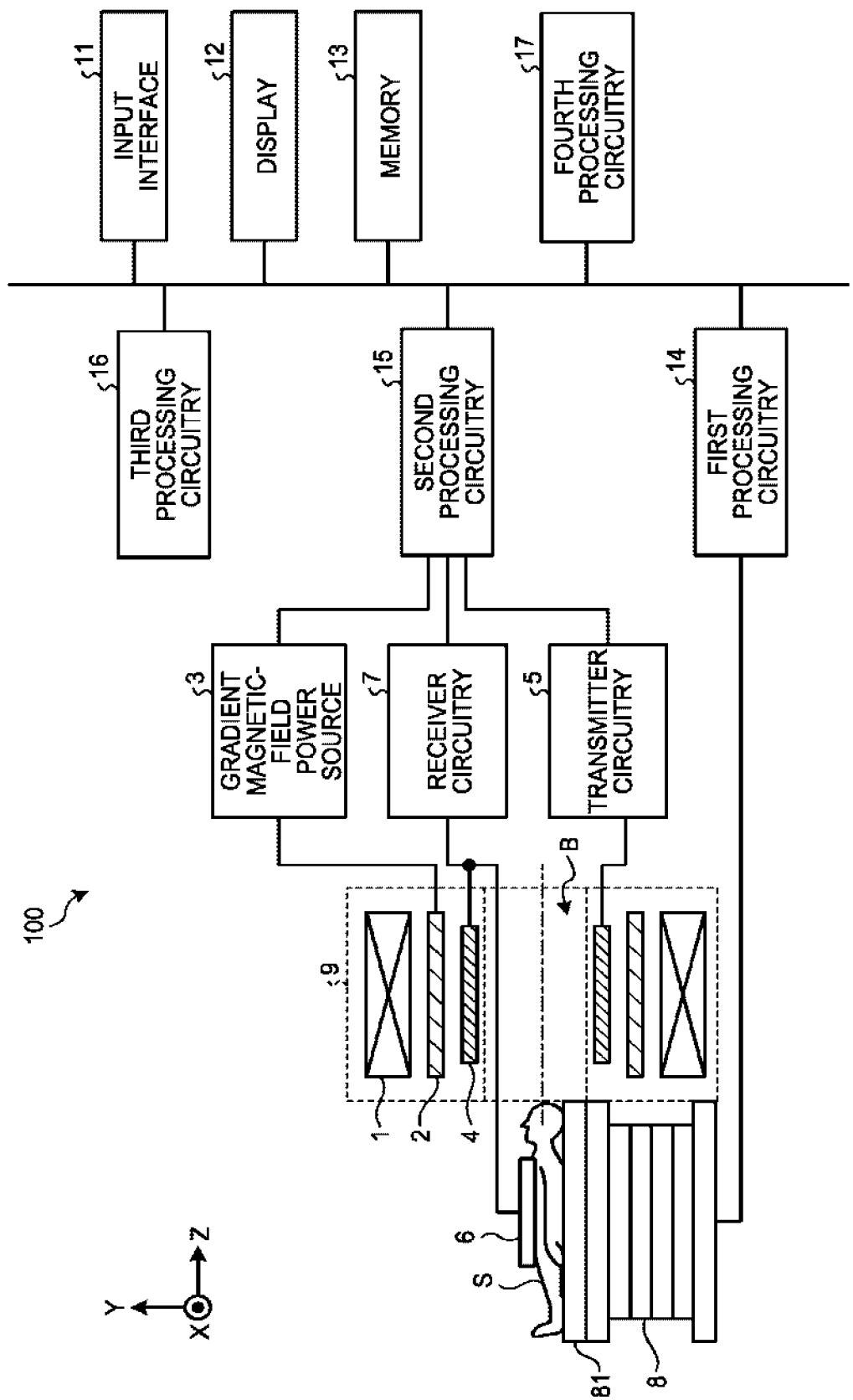
FIG. 1 is a diagram that illustrates an example of the configuration of a magnetic resonance imaging apparatus according to a first embodiment.

Currently, in magnetic resonance imaging, a graphical slice locator is widely used. The graphical slice locator is a graphical interface based on a reference image, which can visualize and define graphical objects of slice sets of magnetic resonance scan etc.

In prior art, a reference image is generally a scanned locator image or a series of obtained images from the same examination of a patient. The locator image is one kind of a reference image, generally one image for each of the coronal plane, the sagittal plane, and the traverse plane of a region respectively. The coronal plane, the sagittal plane, and the traverse plane of the region can be obtained by a specific scan sequence, and these reference images are used for subsequent slice locating and scanning. In the first scan, the locator image is generally used as the reference image, and the resulting images of previous scans can also be employed as the reference image for slice locating of the subsequent scans.

Moreover, current magnetic resonance imaging graphical slice locator commonly employs a two dimensional (2D) graphical locator mode, i.e., the locator images, e.g. the coronal plane, sagittal plane and traverse plane locator images, are displayed on three windows respectively, and by dragging, zooming in, zooming out, adding and deleting the graphical objects using a mouse, the projections of the graphical objects correlated with each other on the locator image plane can be adjusted, and then the location of the graphical object, i.e. the position, orientation etc. on the section plane of the subject can be changed in the three dimensional (3D) space.

However, this existing 2D graphical locator can't provide a 3D reference image to provide an intuitive slice location display to an operator. Therefore, in order to obtain the target graphical slice locator, the adjustment made to the location by the operator will correspondingly change the location of the slice in the 3D space, however, the operator needs to pre-determine by himself whether the position, orientation etc. of the slice in the 3D space meet the requirements and cover the target region (sometimes also referred to as region of interest) based on the projection of the 2D locator image. However, current 2D graphical locator mode has disadvantages, such as the non-intuitive display and manipulate, the long learning period for the beginners, and the difficulty in operation etc. Further, current magnetic resonance imaging graphical locator generally employs the 2D graphical slice locator mode, the operator needs to locate on a 2D plane, while imagine the scene of its back projection to the 3D space. This operation mode is not intuitive and requires repeated adjustment to achieve ideal effect, which has poor operability and is time consuming.

Moreover, recently, technical solutions that improve the above solutions have been developed, i.e. presenting the operation results by 3D visualization, and providing a number of 3D image operation tools to operate these graphical objects directly in the 3D image space.

However, in the improved technical solutions, although a 3D reference image can be obtained, but from such a 3D reference image, only the locating orientation in space can be known, the detailed information at the location can't be acknowledged.

Moreover, recently, in magnetic resonance imaging, the local excitation pulse imaging has become a focus, the future of magnetic resonance imaging will be imaging with a small field of view and high resolution. However, in the current magnetic resonance imaging technology, in order to achieve local excitation pulse imaging with a small field of view and high resolution, the following problems still exist, i.e. lack of detailed information in an intuitive view, and it is only depended on the user's space imagination to make adjustments to perform locating and the next scan; moreover, a precise locating of a small area can't be provided.

Figure 13A:
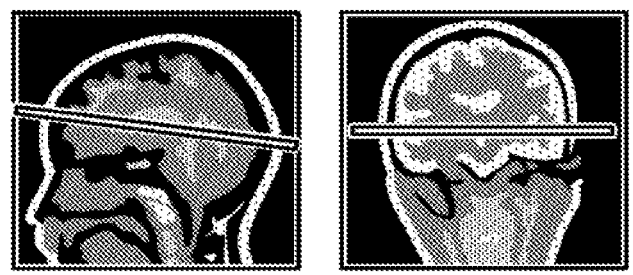
FIG. 13A and FIG. 13B are sketches of the application of the local excitation scan and the non-local excitation scan.

Moreover, in the field of magnetic resonance imaging, the non-local excitation scan is widely used as a general scan. It is generally the case as shown in FIG. 13A that the scan region is larger than the outline of the body (here as the outline of the head) when using a non-local excitation scan, and by using an over-sampling technique, these techniques will hinder a hyperfine effect. Moreover, when using a non-local excitation scan to image a small field of view of imaging area that is smaller than the outline of the human body, there will be wrap artifacts. It can be seen that the imaging effect is not ideal when using non-local excitation scan to image small field-of-view.

Figure 13B:
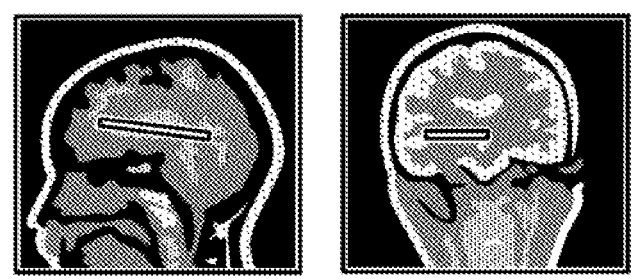

Moreover, the local excitation scan technique utilizing the local excitation pulse imaging can achieve a hyperfine scan, even in the case as shown in FIG. 13B that the scan area is smaller than the outline of the body (here as the outline of the head).

Moreover, FIG. 14 shows an image obtained by applying non-local excitation scan and local excitation scan to scan a small field of view. It can be seen that the image obtained by applying local excitation scan is more hyperfine and clearer.

Moreover, the local excitation scan and the non-local excitation scan correspond to different parameters. Currently, when conducting magnetic resonance imaging, the parameters corresponding to the local excitation scan and the non-local excitation scan is set in advance by the user, and the local excitation scan or non-local excitation scan can be then performed. If it is desired to change the scan mode of the imaging application, the user needs to modify the parameters manually, which is very tedious.

The Embodiments are proposed for resolving the above mentioned problems. The object of the embodiments is to provide a magnetic resonance imaging apparatus, a magnetic resonance imaging method, and a magnetic resonance imaging system, which is capable of providing an intuitive preview. In an aspect of the embodiments, even for locating complicated anatomy structure or small region, it is still capable of locating the region of interest with high precision. Further, in an aspect of the embodiments, an imaging with small field-of-view and high resolution can be achieved by simple operation. In an aspect of the embodiments, it is also capable of automatically switch between the local excitation scan and the non-local excitation scan.

A magnetic resonance imaging apparatus according to an aspect of the embodiments includes a display, an input interface, and processing circuitry. The display is configured to display at least a locator image and a reference image. The input interface is configured to set a region of interest on the locator image displayed on the display. The processing circuitry is configured to scan a subject to obtain three dimensional data, generate a locator image from the three dimensional data and displaying the locator image on the display, generate a reference image corresponding to the location of the region of interest from the three dimensional data and displaying the reference image on the display, and make, when a size or position of the region of interest on one of the locator image and the reference image is changed by the input interface, adjustments to correspondingly change the display magnification or position of the other one of the locator image and the reference image.

Moreover, in the magnetic resonance imaging apparatus according to an aspect of the embodiments, when the reference image is zoomed in or zoomed out, the processing circuitry adjusts the size of the region of interest being set on the locator image so as to correspond to an area of the reference image, the area being displayed by the display after the reference image has been zoomed in or zoomed out, and, when the region of interest being set on the locator image is increased or reduced, the processing circuitry zooms in or zooms out the reference image so as to correspond to the region of interest having been increased or reduced.

Moreover, in the magnetic resonance imaging apparatus according to an aspect of the embodiments, the processing circuitry further scan a part of the subject corresponding to the region of interest to obtain image data.

Moreover, in the magnetic resonance imaging apparatus according to an aspect of the embodiments, the processing circuitry generates a multi-plane reconstruction (MPR) image at a predetermined position and orientation from the three dimensional data, as the locator image.

Moreover, in the magnetic resonance imaging apparatus according to an aspect of the embodiments, the processing circuitry generates a volumetric rendering image rendered from a predetermined orientation from the three dimensional data as the locator image.

Moreover, in the magnetic resonance imaging apparatus according to an aspect of the embodiments, the processing circuitry applies a local excitation scan to obtain two dimensional or three dimensional data of the part corresponding to the region of interest from the subject.

Moreover, in the magnetic resonance imaging apparatus according to an aspect of the embodiments, the processing circuitry further determine whether the size of the region of interest is smaller than a predetermined size, wherein, when determining that the size of the region of interest is within a prescribed range, the processing circuitry performs a local excitation scan, and, when determining that the size of the region of interest is greater than the prescribed range, the processing circuitry performs a non-local excitation scan.

Moreover, in the magnetic resonance imaging apparatus according to an aspect of the embodiments, when determining that the size of the region of interest is smaller than the prescribed range supported by the local excitation scan, the processing circuitry further issues an alert on the display to alert that the local excitation scan cannot be performed.

Moreover, in the magnetic resonance imaging apparatus according to an aspect of the embodiments, when determining that the size of the region of interest is smaller than the prescribed range supported by the local excitation scan, the processing circuitry further issues a message to indicate that the local excitation scan cannot be performed.

Moreover, in the magnetic resonance imaging apparatus according to an aspect of the embodiments, when determining that the size of the region of interest is smaller than the prescribed range supported by the local excitation scan, the processing circuitry further issues a message to indicate that the local excitation scan cannot be performed, and the processing circuitry automatically adjusts the size of the region of interest to turn it into the size within the prescribed range that can be supported.

Moreover, in the magnetic resonance imaging apparatus according to an aspect of the embodiments, the processing circuitry obtains volumetric data as the three dimensional data.

Moreover, in the magnetic resonance imaging apparatus according to an aspect of the embodiments, the processing circuitry obtains a multi-slice image as the three dimensional data.

Moreover, a magnetic resonance imaging method according to an aspect of the embodiments is used by a magnetic resonance imaging apparatus including a display for displaying at least a locator image and a reference image, and the magnetic resonance imaging method includes scanning a subject to obtain three dimensional data; generating a locator image from the three dimensional data and displaying the locator image on the display; setting a region of interest on the locator image displayed by the display; generating a reference image corresponding to the location of the region of interest from the three dimensional data and displaying the reference image on the display; and making, when a size or position of the region of interest on one of the locator image and the reference image is changed, adjustments to correspondingly change the display magnification or position of the other one of the locator image and the reference image.

Moreover, a magnetic resonance imaging system according to an aspect of the embodiments is used by a magnetic resonance imaging apparatus including a display configured to display at least a locator image and a reference image, and the magnetic resonance imaging system includes a first scan means for scanning a subject to obtain three dimensional data; a locator image generation means for generating a locator image from the three dimensional data and displaying the locator image on the display; an input means for setting a region of interest on the locator image displayed on the display; a reference image generation means for generating a reference image corresponding to the location of the region of interest from the three dimensional data and displaying the reference image on the display; and an adjustment means for, when the size or position of the region of interest on one of the locator image and the reference image is changed by the input means, making adjustments to correspondingly change the display magnification or position of the other one of the locator image and the reference image.

By a magnetic resonance imaging apparatus, the magnetic resonance imaging method and the magnetic resonance imaging system according to an aspect of the embodiments, an intuitive preview can be provided. Even in case of locating complicated anatomy structures or small regions, it is still capable of locating the region of interest with high precision. And an imaging of small field-of-view and high resolution can be achieved by simple operations. It is also capable of automatically switch between the local excitation scan and the non-local excitation scan.

In the following, the embodiments will be described with reference to the accompanying drawings. Moreover, the embodiments that will be described in the following are all particular examples of the present invention. Therefore, the values, shapes, sizes, constituent elements, the configured positions of the constituent elements and the way of connection etc. shown in the following embodiments are all examples, and are not intended to limiting the invention. Therefore, among the constituent elements of the following embodiments, the constituent elements not recited in the technical solutions showing the upper-most conceptions, will be described as arbitrary constituent elements.

Moreover, in the figures, substantially identical constituents are assigned with identical symbols, and there are cases that repeated descriptions are omitted or simplified.

First Embodiment

In the following, the magnetic resonance imaging apparatus 100 according to a first embodiment will be described.

FIG. 1 is a diagram that illustrates an example of the configuration of a magnetic resonance imaging apparatus 100 according to the first embodiment. For example, as illustrated in FIG. 1, the Magnetic resonance imaging apparatus 100 includes a static magnetic field magnet 1, a gradient coil 2, a gradient magnetic field power source 3, a transmitter coil 4, transmitter circuitry 5, a receiver coil 6, receiver circuitry 7, a couch 8, gantry 9, an input interface 11, a display 12, memory 13, first processing circuitry 14, second processing circuitry 15, third processing circuitry 16, and fourth processing circuitry 17.

The static magnetic field magnet 1 is formed into a substantially cylindrical shape (including the one that has an elliptical shape in cross-section perpendicular to the central axis of the cylinder) with a hollow, and it generates a uniform static magnetic field in the imaging space that is formed on the inner circumference side. For example, the static magnetic field magnet 1 is implemented by a permanent magnet, a superconductive magnet, or the like.

The gradient coil 2 is formed into a substantially cylindrical shape (including the one that has an elliptical shape in cross-section perpendicular to the central axis of the cylinder) with a hollow, and it is located on the inner circumference side of the static magnetic field magnet 1. The gradient coil 2 includes three coils that generate gradient magnetic fields along the x axis, the y axis, and the z axis, which run at right angles to one another. Here, the x axis, the y axis, and the z axis constitute the apparatus coordinate system that is unique to the Magnetic resonance imaging apparatus 100. For example, the direction of the x axis is set in the vertical direction, and the direction of the y axis is set in the horizontal direction. Furthermore, the direction of the z axis is set in the same direction as that of the magnetic flux of the static magnetic field that is generated by the static magnetic field magnet 1.

The gradient magnetic field power source 3 individually supplies the current to each of the three coils, included in the gradient coil 2, thereby generating a gradient magnetic field in the imaging space along each of the x axis, the y axis, and the z axis. By generating a gradient magnetic field along each of the x axis, the y axis, and the z axis as appropriate, gradient magnetic fields may be generated along a read-out direction, a phase encode direction, and a slice direction, which are perpendicular to one another. Here, the axes along the read-out direction, the phase encode direction, and the slice direction constitute a logical coordinate system that defines a slice area or a volume area, which is the target to be imaged. Furthermore, hereinafter, the gradient magnetic field along the read-out direction is referred to as a read-out gradient magnetic field, a gradient magnetic field along the phase encode direction is referred to as a phase-encode gradient magnetic field, and the gradient magnetic field along the slice direction is referred to as the slice gradient magnetic field.

Here, each of the gradient magnetic fields is overlapped with a static magnetic field that is generated by the static magnetic field magnet 1, and it is used to give spatial positional information to magnetic resonance signals (magnetic resonance: MR). Specifically, the read-out gradient magnetic field changes the frequency of the MR signal in accordance with the position in the read-out direction so as to give the positional information along the read-out direction to the MR signal. Furthermore, the phase-encode gradient magnetic field changes the phase of the MR signal along the phase encode direction so as to give the positional information in the phase encode direction to the MR signal. Furthermore, the slice gradient magnetic field is used to determine the direction of a slice area, the thickness, or the number of pieces if the imaging area is a slice area and, if the imaging area is a volume area, it changes the phase of the MR signal in accordance with the position in the slice direction so as to give the positional information along the slice direction to the MR signal.

The transmitter coil 4 is formed into a substantially cylindrical shape (including the one that has an elliptical shape in cross-section perpendicular to the central axis of the cylinder) with a hollow, and it is located inside the gradient coil 2. The transmitter coil 4 applies radio frequency (RF) pulses, output from the transmitter circuitry 5, to the imaging space.

The transmitter circuitry 5 outputs RF pulses, which correspond to the Larmor frequency, to the transmitter coil 4. For example, the transmitter circuitry 5 includes an oscillation circuit, a phase selection circuit, a frequency conversion circuit, an amplitude modulation circuit, and an RF amplification circuit. The oscillation circuit generates RF pulses at the resonant frequency that is unique to the target atomic nucleus, which is placed in the static magnetic field. The phase selection circuit selects the phase of the RF pulse that is output from the oscillation circuit. The frequency conversion circuit converts the frequency of the RF pulse that is output from the phase selection circuit. The amplitude modulation circuit modulates the amplitude of the RF pulse, output from the frequency conversion circuit, in accordance with for example sinc function. The RF amplification circuit amplifies the RF pulse, output from the amplitude modulation circuit, and outputs it to the transmitter coil 4.

The receiver coil 6 is an RF coil that receives an MR signal that is emitted from the subject S. Specifically, the receiver coil 6 is an RF coil that is worn by the subject S who is placed in the imaging space and receives the MR signal that is emitted from the subject S because of the effect of the RF magnetic field that is applied by the transmitter coil 4. The receiver coil 6 outputs the received MR signal to the receiver circuitry 7. For example, a dedicated coil is used as the receiver coil 6 for each region to be imaged. The dedicated coil may be, for example, a receiver coil for head, a receiver coil for cervix, a receiver coil for shoulder, a receiver coil for breast, a receiver coil for abdomen, a receiver coil for lower extremity, a receiver coil for spine.

The receiver circuitry 7 generates MR signal data on the basis of the MR signal, output from the receiver coil 6, and outputs the generated MR signal data to the second processing circuitry 15. For example, the receiver circuitry 7 includes a selection circuit, a former-stage amplification circuit, a phase detection circuit, and an analog-digital conversion circuit. The selection circuit selectively inputs MR signals that are output from the receiver coil 6. The former-stage amplification circuit amplifies MR signals that are output from the selection circuit. The phase detection circuit detects the phase of the MR signal that is output from the former-stage amplification circuit. The analog-digital conversion circuit converts analog signals, output from the phase detection circuit, into digital signals to generate MR signal data, and it outputs the generated MR signal data to the second processing circuitry 15.

Furthermore, an explanation is given here of an example of the case where the transmitter coil 4 applies RF pulses and the receiver coil 6 receives MR signals; however, the configurations of the transmitter coil 4 and the receiver coil 6 are not limited thereto. For example, the transmitter coil 4 may further have a receiving function to receive MR signals. Furthermore, the receiver coil 6 may further have a transmitting function to apply an RF magnetic field. If the transmitter coil 4 has a receiving function, the receiver circuitry 7 also generates MR signal data from MR signals that are received by the transmitter coil 4. Furthermore, if the receiver coil 6 has a transmitting function, the transmitter circuitry 5 also outputs RF pulses to the receiver coil 6.

The couch 8 includes a couchtop 81, on which the subject S is placed and, when capturing is conducted on the subject S, it inserts the couchtop 81 into the imaging space that is formed inside the static magnetic field magnet 1 and the gradient coil 2. For example, the couch 8 is arranged such that its longitudinal direction is parallel to the central axis of the static magnetic field magnet 1.

The gantry 9 accommodates the static magnetic field magnet 1, the gradient coil 2, and the transmitter coil 4. Specifically, the gantry 9 includes a bore B formed in a cylinder shape, and accommodates the static magnetic field magnet 1, the gradient coil 2, and the transmitter coil 4 so that the static magnetic field magnet 1, the gradient coil 2, and the transmitter coil 4 are each arranged so as to surround the bore B. Here, the space inside of the bore B included in the gantry 9 serves as an imaging space where the subject S is placed when an imaging thereof is performed.

The input interface 11 receives input operations of various types of commands and various types of information from an operator. Specifically, the input interface 11 is connected to the fourth processing circuitry 17 so that it converts the input operation, received from an operator, into an electric signal and outputs it to the fourth processing circuitry 17. For example, the input interface 11 is implemented by a trackball, a switch button, a mouse, a keyboard, a touch pad for receiving input operations through touching operations to an operation screen thereof, a touch screen in which a display screen and a touch pad are integrated, a noncontact input circuit using an optical sensor, a voice input circuit, or the like, used for setting imaging conditions and region of interest, etc. Here, in this specification, it is noted that the input interface 11 is not limited to a device which includes a physical component for receiving an operation, such as the mouse and the keyboard. For example, an electrical signal processing circuit configured to receive electrical signals corresponding to the input operations from an external input device provided separately from the apparatus, and to output the electrical signals to the fourth processing circuitry 17 is included in examples of the input interface 11.

The display 12 displays various types of information and various images. Specifically, the display 12 is connected to the fourth processing circuitry 17 so that it converts the data on various types of information and various images, transmitted from the fourth processing circuitry 17, into electric signals for display and outputs them. For example, the display 12 is implemented by a liquid crystal monitor, a cathode ray tube (CRT) monitor, a touch panel, or the like.

The memory 13 stores various types of data. Specifically, the memory 13 stores MR signal data or image data for each of the subjects S. For example, the memory 13 is implemented by a semiconductor memory device, such as a random access memory (RAM) or a flash memory, a hard disk, an optical disk, or the like.

The first processing circuitry 14 has a bed control function. Specifically, the first processing circuitry 14 is connected to the couch 8 so that it outputs electric signals for control to the couch 8, thereby controlling operations of the couch 8. For example, the first processing circuitry 14 receives a command to move the couchtop 81 in the longitudinal direction, the vertical direction, or the horizontal direction from an operator via the input interface 11, and it operates a driving mechanism for the couchtop 81, included in the couch 8, to move the couchtop 81 in accordance with the received command. For example, the first processing circuitry 14 is implemented by a processor.

The second processing circuitry 15 has an execution function. Specifically, the second processing circuitry 15 conducts various pulse sequences. That is, the second processing circuitry 15 drives the gradient magnetic field power source 3, the transmitter circuitry 5, and the receiver circuitry 7 on the basis of the sequence execution data, output from the processing circuitry 15, thereby conducting various pulse sequences. For example, the second processing circuitry 15 is implemented by a processor.

Here, the sequence execution data is the information that defines the pulse sequence that indicates the procedure for acquiring MR signal data. Specifically, the sequence execution data is the information that defines the timing in which the gradient magnetic field power source 3 supplies current to the gradient coil 2 and the level of the supplied current, the level of the RF pulse current, which is supplied to the transmitter coil 4 by the transmitter circuitry 5 and the supply timing, the detection timing in which the receiver circuitry 7 detects MR signals, or the like.

Furthermore, as a result of execution of various pulse sequences, the second processing circuitry 15 receives MR signal data from the receiver circuitry 7 and stores the received MR signal data in the memory 13. Furthermore, the set of MR signal data, received by the second processing circuitry 15, is arranged in two dimensions or three dimensions in accordance with the positional information, which is given by the read-out gradient magnetic field, the phase-encode gradient magnetic field, and the slice gradient magnetic field, described above, so that it is stored as the data that forms the k space in the memory 13.

The third processing circuitry 16 has a data processing function. For example, the third processing circuitry 16 is implemented by a processor. The third processing circuitry 16 generates images on the basis of the MR signal data that is stored in the memory 13. Specifically, the third processing circuitry 16 reads the MR signal data that is stored in the memory 13 by the second processing circuitry 15 and performs post-processing, i.e., reconstruction process, such as Fourier transform, on the read MR signal data to generate images. Furthermore, the third processing circuitry 16 stores the image data on the generated image in the memory 13.

The fourth processing circuitry 17 controls each component included in the Magnetic resonance imaging apparatus 100, thereby performing the overall control on the Magnetic resonance imaging apparatus 100. For example, the fourth processing circuitry 17 is implemented by a processor. For example, the fourth processing circuitry 17 15 receives inputs of various parameters with regard to the pulse sequence from an operator via the input interface 11 and, in accordance with the received parameter, generates sequence execution data. Then, the fourth processing circuitry 17 transmits the generated sequence execution data to the processing circuitry 13, thereby conducting various pulse sequences. Furthermore, for example, the fourth processing circuitry 17 reads the image data on an image, which is requested by an operator, from the memory 13 and outputs the read image to the display 12.

[Constituents of the Magnetic Resonance Imaging Apparatus 100]

Figure 2:
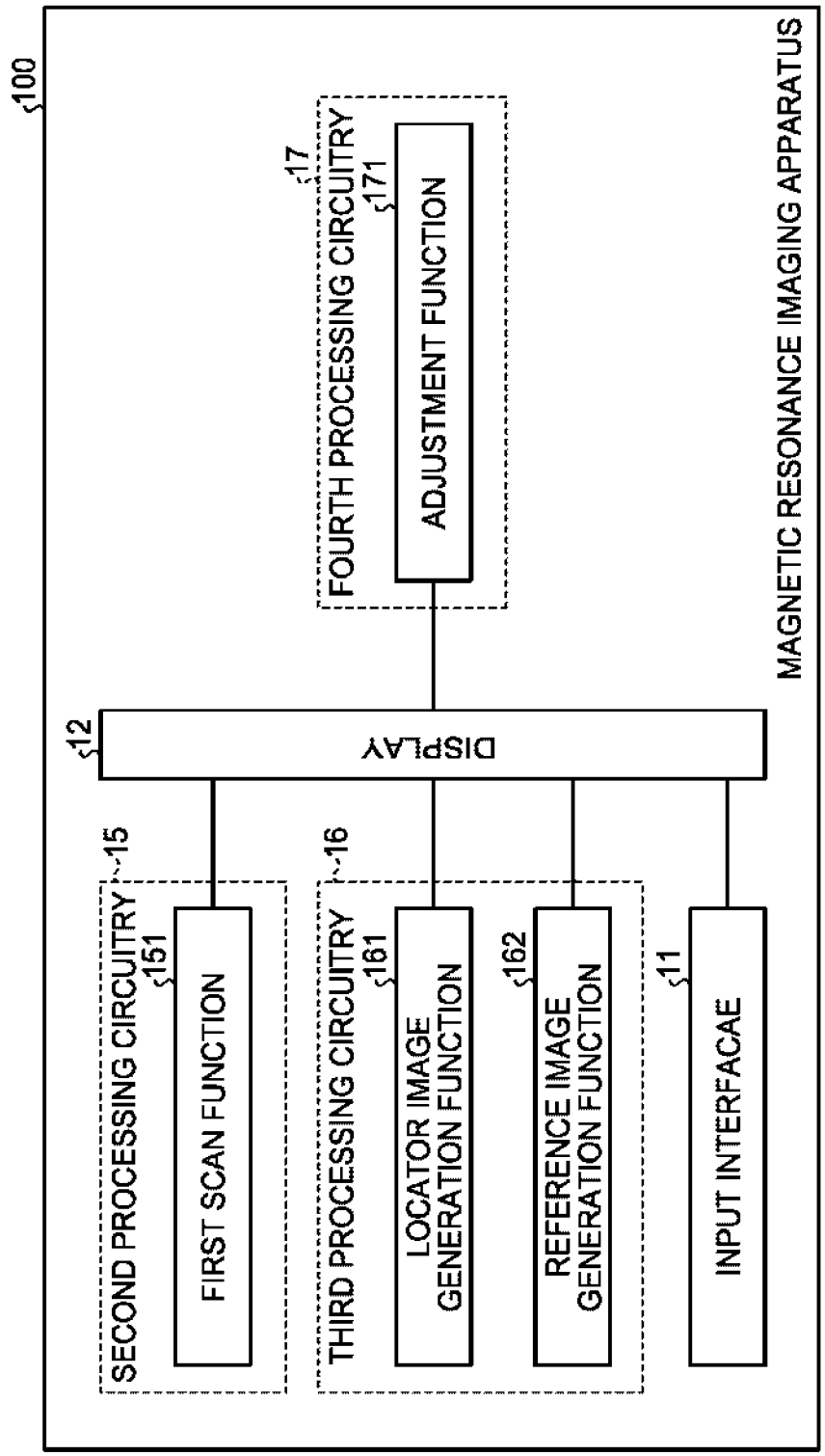
FIG. 2 is a block diagram of the magnetic resonance imaging apparatus according to the first embodiment.
Figure 3:
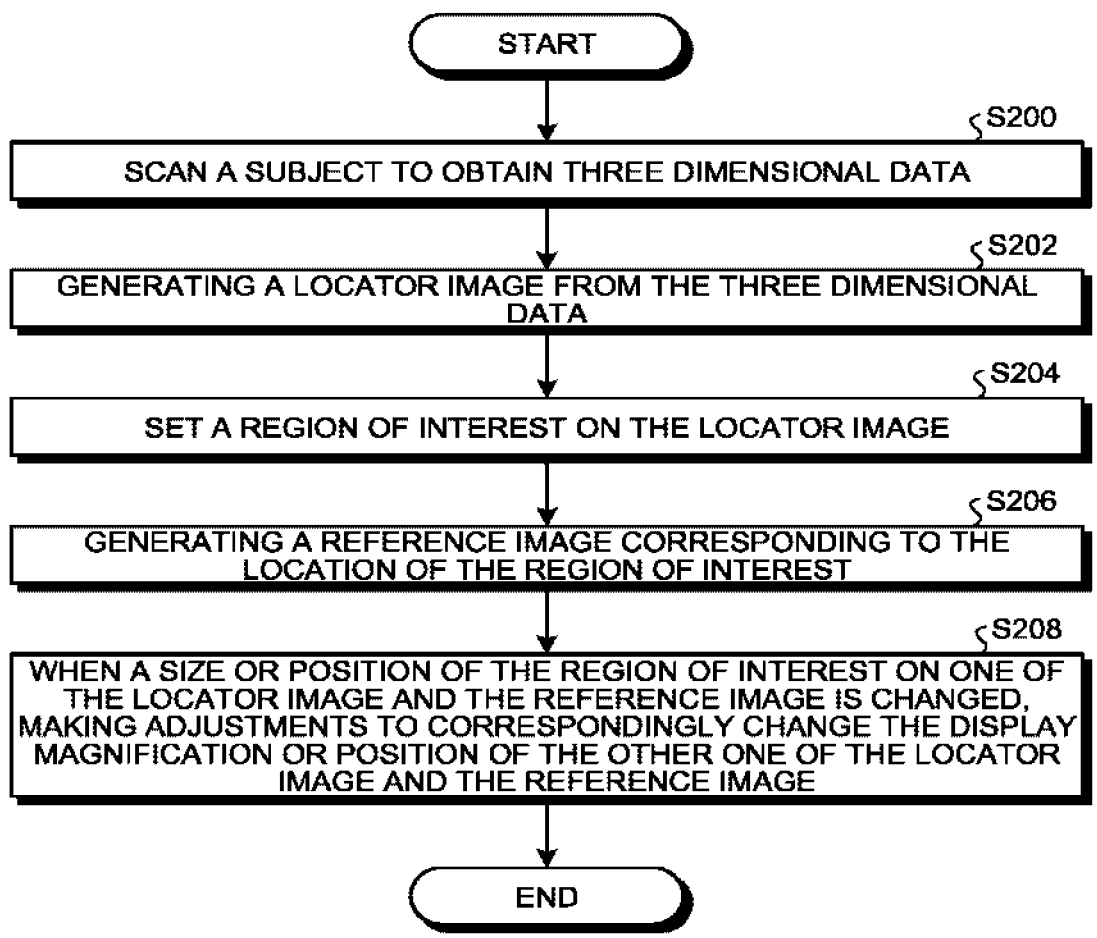
FIG. 3 is a flow diagram of the magnetic resonance imaging method performed by the magnetic resonance imaging apparatus according to the first embodiment.
Figure 4:
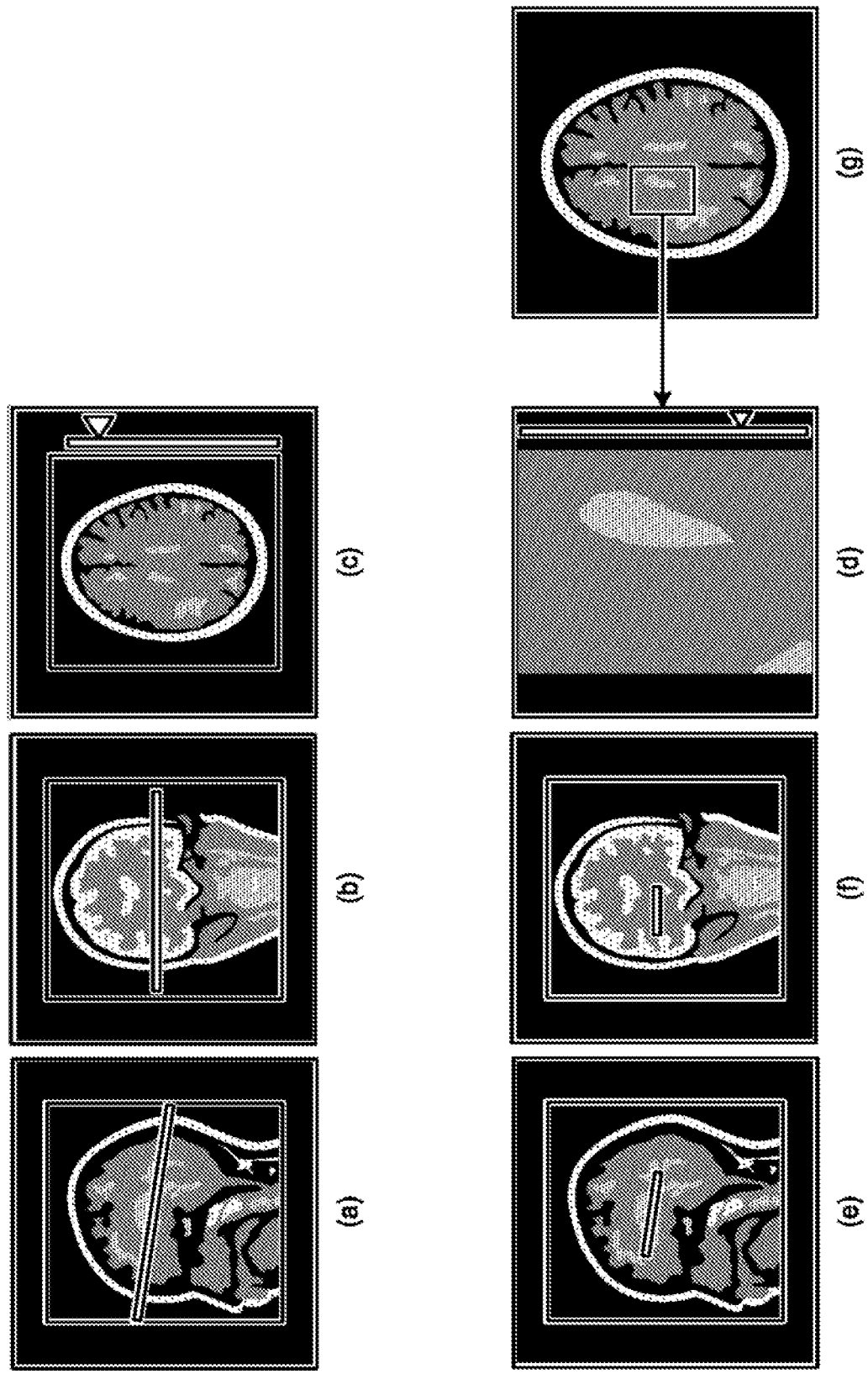
FIG. 4 is a schematic view of an example display of the magnetic resonance imaging apparatus according to the first embodiment.

In the following, the magnetic resonance imaging apparatus 100 according a first embodiment will be described with reference to FIG. 2 to FIG. 4. FIG. 2 is a block diagram of the magnetic resonance imaging apparatus 100 according to the first embodiment. FIG. 3 is a flow diagram of the magnetic resonance imaging method performed by the magnetic resonance imaging apparatus 100 according to the first embodiment. FIG. 4 is a schematic view of an example display of the magnetic resonance imaging apparatus 100 according to the first embodiment.

Further, the magnetic resonance imaging apparatus 100 includes various components, only the components related to the technical idea of the invention are shown, and other components are omitted.

As shown in FIG. 2, the magnetic resonance imaging apparatus 100 comprises the display 12, a first scan function 151, a locator image generation function 161, the input interface 11, a reference image generation function 162 and an adjustment function 171.

In this embodiment, the second processing circuitry 15 includes the first scan function 151, the third processing circuitry 16 includes the locator image generation function 161 and the reference image generation function 162, and the fourth processing circuitry 17 includes the adjustment function 171.

The display 12 consists of for example a CRT (Cathode Ray Tube) display, a liquid crystal display, and has display function. For example, it is capable of displaying at least a locator image and a reference image.

The first scan function 151 scans the subject of the magnetic resonance imaging (simplified as subject in the following), e.g. a head of a person, to obtain a 3D data of the subject. The first scan function 151 can obtain volumetric data as the 3D data. Moreover, the first scan function 151 can also obtain a multi-slice image as the 3D data.

The locator image generation function 161 generates a locator image from the 3D data obtained by the first scan function 151 and sends the generated locator image to the display 12 to display with a suitable display magnification. The locator image generation function 161 can generate a multi-plane reconstruction MPR image at a predetermined position and orientation from the 3D data as the locator image. Moreover, the locator image generation function 161 can also generate a volumetric rendering image rendered from a predetermined orientation from the 3D data as the locator image.

The input interface 11 is a device that is capable of input, which can be a mouse, a keyboard, a joystick, a trackball, a touch screen, a light pen, a language controller etc. The input interface 11 sets a region of interest ROI on the locator image displayed by the display 12 according to the operation of the user such as a doctor. Here, a region of interest refers to the region on which the scan will performed.

The reference image generation function 162 generates a reference image associated with the location of the region of interest ROI from the 3D image obtained by the first scan function 151, and sends the generated reference image to the display 12 for display with a suitable display magnification.

The adjustment function 171, when the size or position of the region of interest ROI on one of the locator image and the reference image is changed by the user such as a doctor via the input interface 11, makes adjustments to accordingly change the display magnification or position of the other one of the locator image and the reference image.

[Magnetic Resonance Imaging Method 100 Performed by the Magnetic Resonance Imaging Apparatus]

Figure 5:
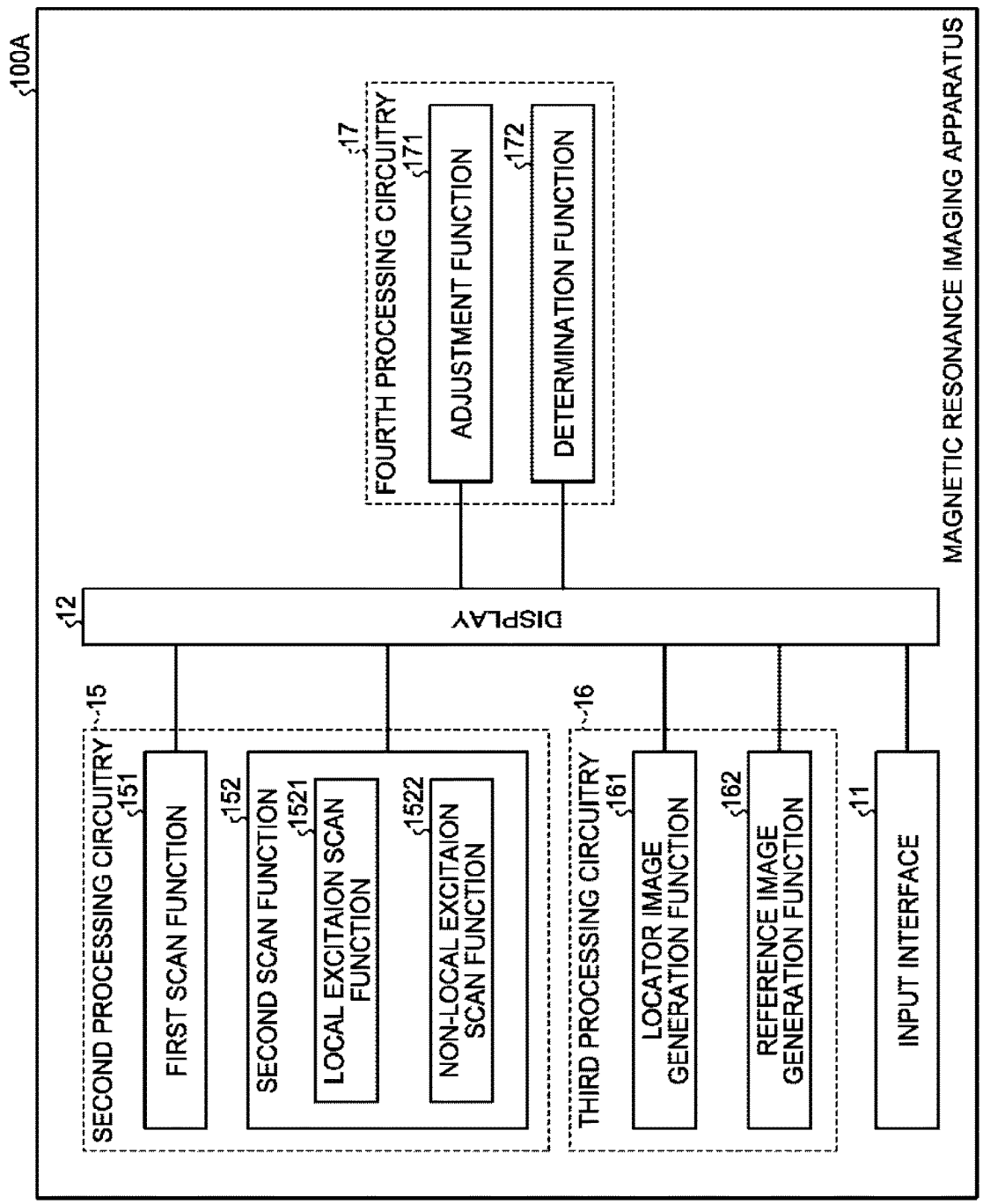
FIG. 5 is a block diagram of the magnetic resonance imaging apparatus according to a second embodiment.

In the following, the magnetic resonance imaging method performed by the magnetic resonance imaging apparatus 100 will be described with reference to FIG. 3 and FIG. 4, wherein FIG. 5 shows a particular example of applying the magnetic resonance imaging apparatus 100 for imaging a human brain.

As shown in FIG. 3, when the magnetic resonance imaging apparatus 100 starts to work, first, in a step S200, the subject, i.e. the head of a human, is scanned by the first scan function 151, so as to obtain 3D data associated with the subject, and thereafter, it is proceeded to step S202.

Next, in step S202, the locator image generation function 161, from the 3D data obtained by the first scan function 151, generates for example the locator image as shown in the images in FIG. 4(a), (b) that does not include the white solid line, and displays the generated locator images at a suitable display magnification by the display 12, and then it is proceeded to step S204. Here, (a) and (b) in FIG. 4 are two locator images of the same object with different views, FIG. 4(a) is a locator image in the sagittal plane, and FIG. 4(b) is a locator image in the coronal plane.

Next, in step S204, a user such as a doctor sets the region of interest ROI on the locator image, by operating the input interface 11, and then it is proceeded to step S206. Here, after setting the region of interest ROI on the locator image, as shown in FIG. 4(a), (b), the region of interest ROI is represented by a white solid line.

Next, in step S206, a reference image corresponding to the location of the region of interest ROI is generated by the reference image generation function 162 from the 3D data obtained by the first scan function 151, and is displayed with a suitable display magnification by the display 12, and then it is proceeded to step S208. Here, the reference image is as shown in FIG. 4(c).

Next, in step S208, when the size or position of the region of interest ROI on one of the locator image and the reference image is changed by the user such as a doctor via the input interface 11, the adjustment function 171 makes adjustments to accordingly change the display magnification or location of the other one of the locator image and the reference image, and then the operation ends.

The first example according to the first embodiment will be described with reference to FIG. 4. In the case of zoom-out operation or zoom-in operation to the reference image (FIG. 4(c)) displayed by the display 12 through the input interface 11, for example, in this embodiment, a zoom-in operation, i.e., by dragging the arrow cursor in the right side of FIG. 4(c) to zoom in the reference image (FIG. 4(c)), the adjustment function 171 adjusts the display magnification of the locator image (FIG. 4(a), (b)) displayed by the display 12, to adjust the size of the region of interest ROI (i.e. the white solid line) set on the locator image, so that they become as shown in FIG. 4(e), (f) respectively, in correspondence with the regions in the reference image (FIG. 4(d)) displayed by the display 12 after the zoom-in operation. Here, the white box in FIG. 4(g) is the region of the reference image displayed in FIG. 4(d).

Further, FIG. 4 shows a case that the user zooms in the reference image by the input interface 11, but in case of a zooming out operation to the reference image as required, the first embodiment of the invention is also applicable (not shown).

By the magnetic resonance imaging apparatus 100 of the first particular example according to the first embodiment, a user, by the simple zoom-in or zoom-out operation, is able to adjust the display magnification of the locator image while locating the region of interest with the reference image at high precision, so as to adjust the size of the region of interest in the locator image. As such, in comparison with the situation in prior arts that requires locating or adjusting the region of interest based on the user's imagination, the user can intuitively locate the region of interest at high precision by the reference image. This is very meaningful for magnetic resonance imaging of small areas, complex or the detailed anatomical structures, etc.

Further, the second example according to the first embodiment will be described with reference to FIG. 4. In the case that the user increases or reduces the region of interest ROI set on the locator image displayed via the display 12 by the input interface 11, the adjustment function 171 conducts the zoom-out operation or the zoom-in operation to the reference image displayed by the display 12, such that the region of the reference image displayed by the display 12 corresponds to the increased or reduced region of interest ROI. Specifically, when the user conducts increasing or reducing (in this embodiment, reducing) to the region of interest ROI (i.e. the white solid line) of the locator image shown in FIGS. 4(a) and (b) by the input interface 11, the adjustment function 171 zooms in the picture shown in FIG. 4(c), such that the reduced region corresponding to the region of interest and as shown in the white box in the reference image of FIG. 4(g) is displayed on the display 12.

Further, FIG. 4 shows that the user reduces the region of interest in the locator image by the input interface 11, but in case that it is needed to increase the region of interest in the locator image, the above first embodiment of the present invention is also applicable (illustration is omitted).

By the magnetic resonance imaging apparatus 100 of the second example according to the first embodiment, when the user simply reduces or increases the region of interest in the locator image, the display magnification for displaying the reference image on the display 12 can be adjusted simultaneously to adjust the size of the region of interest. An intuitive reference image information can be provide for the user determination, so as to facilitate the user to determine whether the currently located region of interest is the region of interest as the user desired, thereby to locate the desired region of interest conveniently and with high precision. Identical to the above first particular example, in comparison with the situation in prior arts that requires locating or adjusting the region of interest based on the user's imagination, the user can intuitively locate the region of interest at high precision by the reference image. This is very meaningful for magnetic resonance imaging of small areas, complex or the detailed anatomical structures etc.

Second Embodiment

Figure 6:
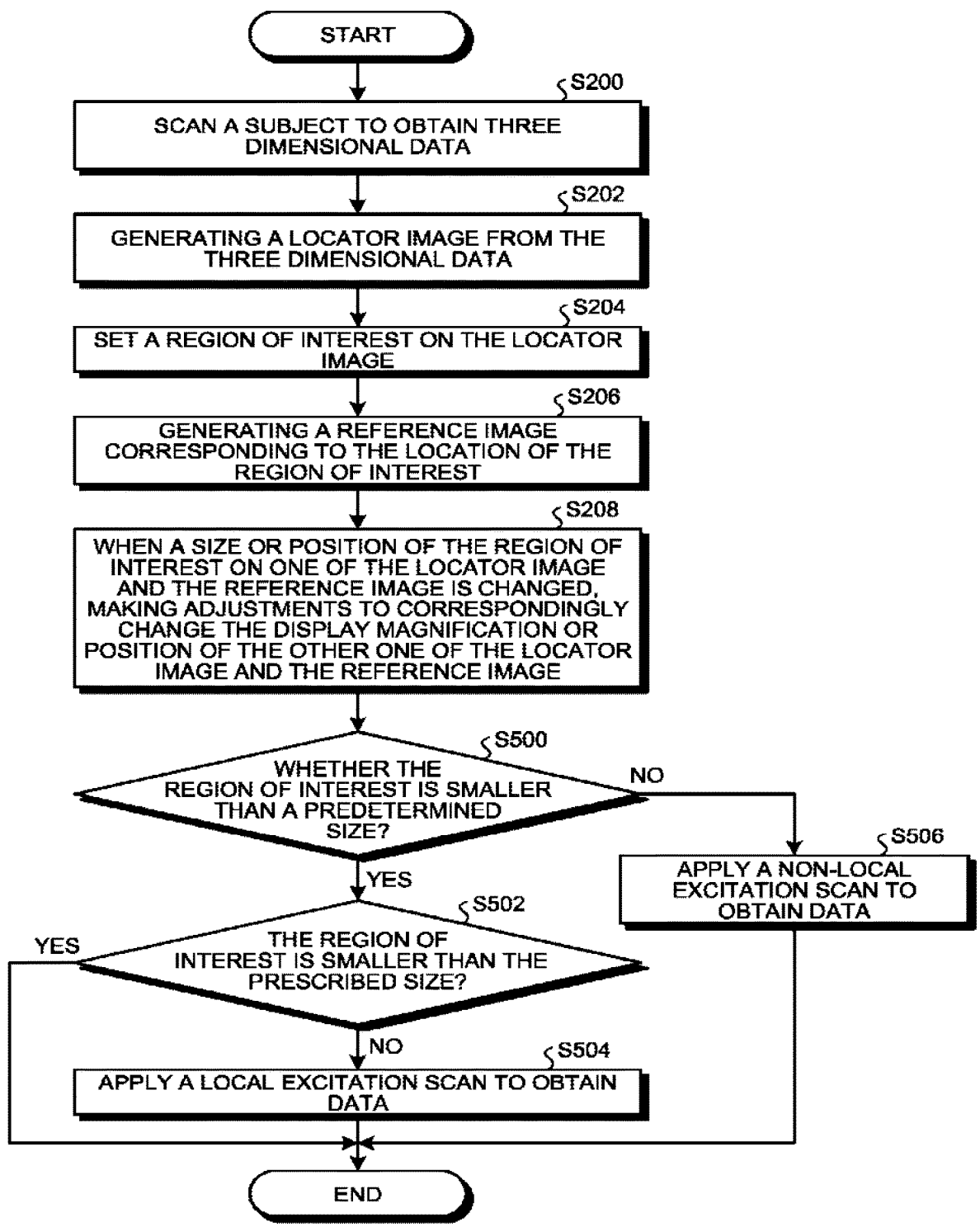
FIG. 6 is a flow diagram of the magnetic resonance imaging method performed by the magnetic resonance imaging apparatus according to the second embodiment.

In the following, the magnetic resonance imaging apparatus 100A according a second embodiment will be described with reference to FIG. 5 to FIG. 6. FIG. 5 is a block diagram of the magnetic resonance imaging apparatus 100A according to the second embodiment. FIG. 6 is a flow diagram of the magnetic resonance imaging method performed by the magnetic resonance imaging apparatus 100A according the second embodiment.

[Constituents of the Magnetic Resonance Imaging Apparatus 100A]

As compared with the magnetic resonance imaging apparatus 100A according to the first embodiment shown in FIG. 2, the magnetic resonance imaging apparatus 100A according to the second embodiment shown in FIG. 5 further comprises a determination function 172 and a second scan function 152. Further, in the present embodiment, the description of the constituents that are identical to the magnetic resonance imaging apparatus 100 is omitted.

In this embodiment, the second processing circuitry 15 further includes the second scan function 152, and the fourth processing circuitry 17 further includes the determination function 172.

The determination function 172 may consist of a CPU or MCU etc., for determining whether the size of the region of interest is less than a predetermined size (e.g., predetermined area).

A second scan function 152 scans the part of the subject corresponding to the region of interest ROI to obtain image data as the imaging data. Moreover, as shown in FIG. 5, the second scan function 152 comprises a local excitation scan function 1521 for performing local excitation scan and a non-local excitation scan function 1522 for performing non-local excitation scan. Moreover, the second scan function 152 can apply a local excitation scan to obtain 3D or 3D data of the part corresponding to the region of interest from the subject.

Moreover, when the determination function 172 determines that the size of the region of interest is within a prescribed range, the local excitation scan function 1521 performs a local excitation scan, and when the determination function 172 determines that the size of the region of interest is larger than the prescribed range, the non-local excitation scan function 1522 performs a non-local excitation scan. Here, the prescribed range refers to a range that can be supported by the local excitation scan, that is, the local excitation scan can be performed only within this range, and when this range is exceeded, the local excitation scan can't be applied. Further, when setting the upper limit of the prescribed range as a predetermined size, and setting the lower limit of the prescribed range as a prescribed size, determining by determination function 172 whether the size of the region of interest is within the prescribed range, can be determined for example by two determinations. Specifically, it can be determined by the determination function 172 whether the size of the region of interest is smaller than the upper limit of the prescribed range, i.e. the predetermined size, and then it is determined by determination function 172 whether the size of the region of interest is smaller than the lower limit of the prescribed range, i.e. the prescribed size. When it is determined by the determination function 172 that the size of the region of interest is smaller than the upper limit of the prescribed range i.e. the predetermined size and not smaller than the lower limit of the prescribed range i.e. the prescribed size, it can be regarded that the size of the region of interest is within the prescribed range. Of course, no particular limit is made to the order of comparing the size of the region of interest with the upper limit and the lower limit of the prescribed range.

[Magnetic Resonance Imaging Method Performed by the Magnetic Resonance Imaging Apparatus 100A]

The magnetic resonance imaging method performed by the magnetic resonance imaging apparatus 100A will be described with reference to FIG. 6. Here, for steps that are identical to the steps in the flowchart shown in FIG. 3, the same reference numerals are assigned and detailed description thereof will be omitted.

As shown in FIG. 6, after the magnetic resonance imaging apparatus 100A of the present embodiment starts to work, the actions of steps S200-S208 are performed identically to the magnetic resonance imaging apparatus 100 of the first embodiment, and after the action of step S208 ends, it is proceeded to step S500.

Next, in step S500, the size of the region of interest ROI adjusted in step S208 is determined by the determination function 172 whether it is less than a predetermined size. Here, the predetermined size may be, for example, the area surrounded by the outer contour of the scanned object. Depending on differences of the scanned objects, the predetermined sizes may be of different values.

When the determination function 172 determines that the size of the region of interest ROI is smaller than the predetermined size (YES in step S500) in step S500, in the next step S502, the determination function 172 further determines whether the size of the region of interest ROI is smaller than the prescribed size. Here, the prescribed size is a lower limit of the prescribed range that a local excitation scanning can be performed. When it is determined that the size of the region of interest ROI is not less than the prescribed size (NO in step S502), it is proceeded to step S504, a local excitation scan is performed by a local excitation scan function 1521 of the second scan section 107 to obtain the data, and then the process ends. Further, when it is determined in step S502 that the size of the region of interest ROI is smaller than the prescribed size (YES in step S502), the local excitation scan can't be performed any more, and therefore the process ends. Further, depending on differences of the scanned objects, the prescribed sizes may be of different values.

On the other hand, in step S500, when the determination function 172 determines that the size of the region of interest ROI is not smaller than the predetermined size, that is, the size of the region of interest ROI is larger than the prescribed range (NO in step S500), it is proceeded to the next step S506, and the non-local excitation scan function 1522 of the second scan function 152 performs a non-local excitation scan to obtain the data, and then the process ends.

The magnetic resonance imaging apparatus 100A of the first action example according to the second embodiment, in addition to having the effects of the above described first embodiment, because of the comparison between the size of the region of interest ROI adjusted by the adjustment function 171 and the range that can be supported by the local excitation scan i.e. the prescribed range, and depending on the result of the comparison, a local excitation scan or non-local excitation scan can be automatically switched and applied. Therefore, as compared with the prior art, without requiring the user to change or set the parameters manually to switch the scan mode, it can automatically select the appropriate scan mode, and thereby reduce user operation and improve the convenience of operating the magnetic resonance imaging apparatus 100A.

Third Embodiment

Figure 7:
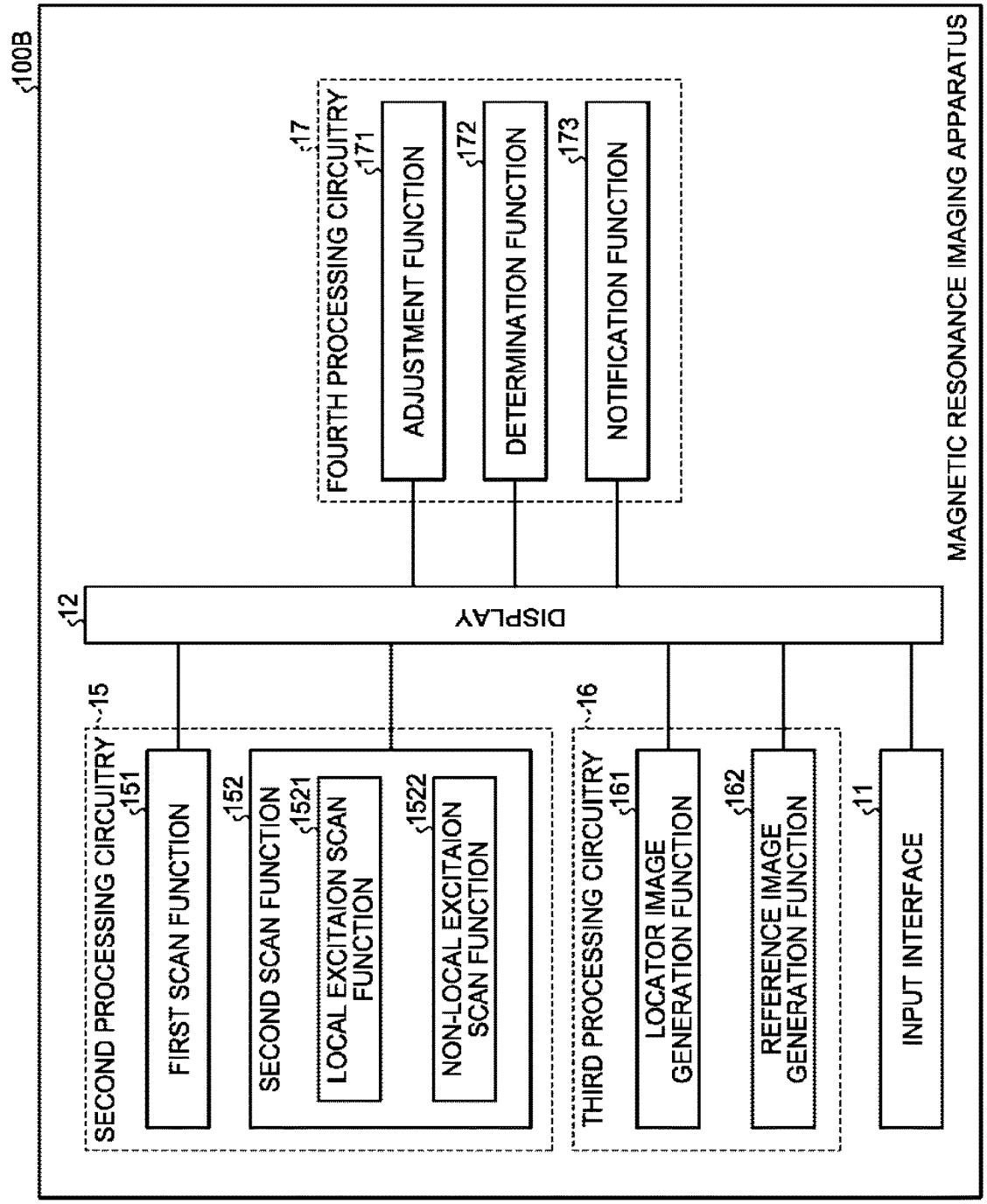
FIG. 7 is a block diagram of the magnetic resonance imaging apparatus according to a third embodiment.
Figure 8:
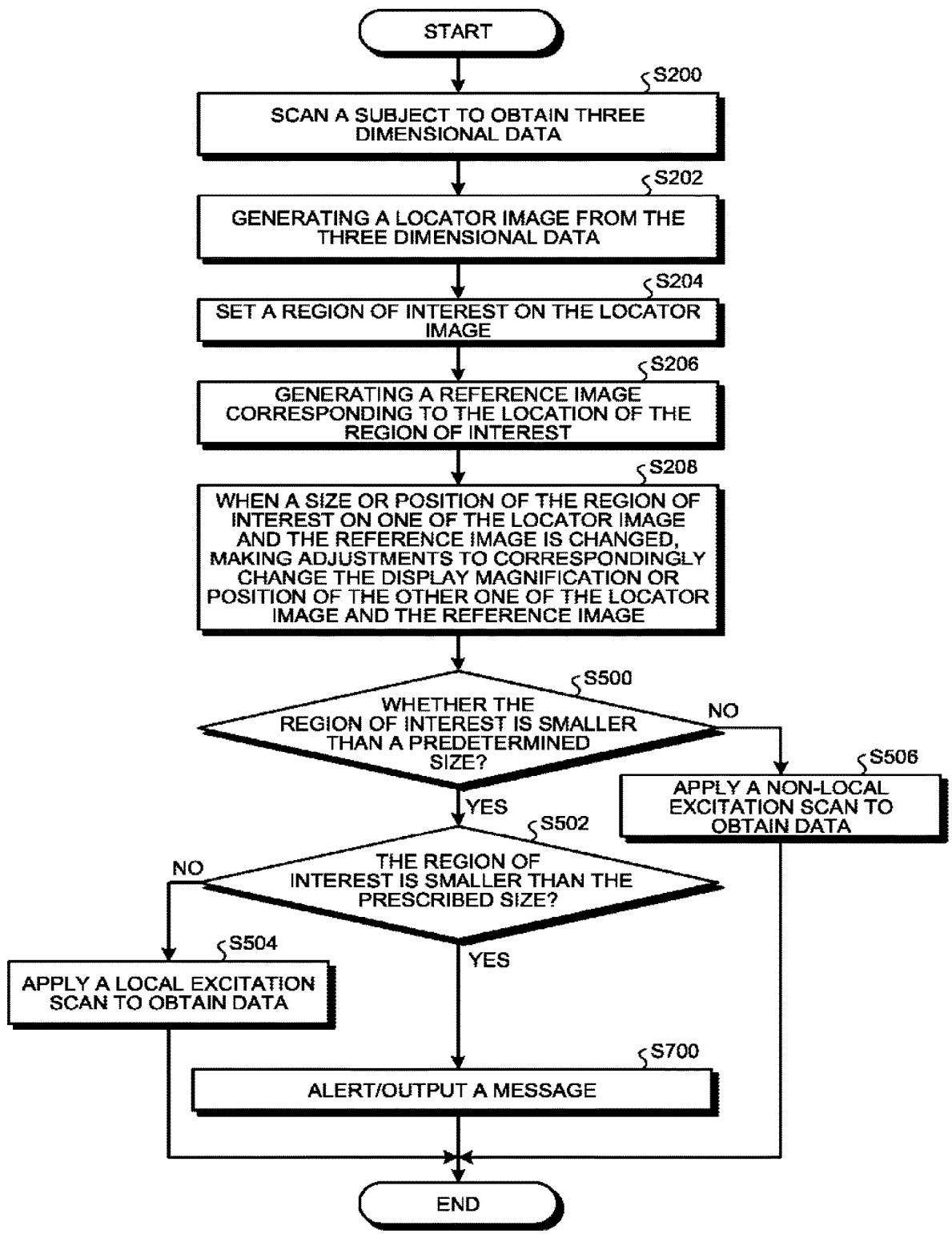
FIG. 8 is a flow diagram of the magnetic resonance imaging method performed by the magnetic resonance imaging apparatus according to the third embodiment.
Figure 9:
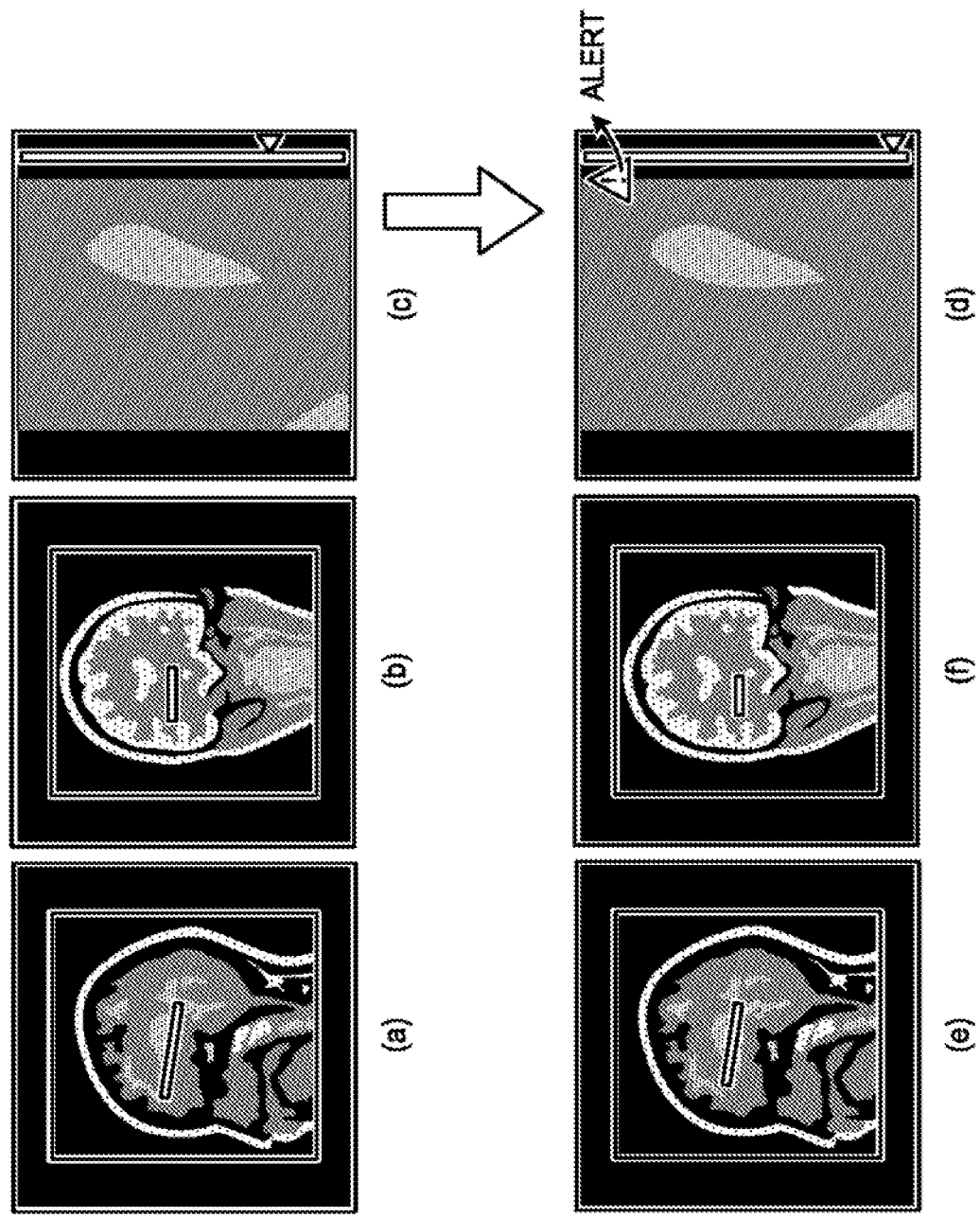
FIG. 9 is a schematic view of an example display of the magnetic resonance imaging apparatus according to the third embodiment.

In the following, the magnetic resonance imaging apparatus 100B according to a first embodiment will be described with reference to FIG. 7 to FIG. 9. FIG. 7 is a block diagram of the magnetic resonance imaging apparatus 100B according to the third embodiment. FIG. 8 is a flow diagram of the magnetic resonance imaging method performed by the magnetic resonance imaging apparatus 100B according to the third embodiment. FIG. 9 is a schematic view of an example display of the magnetic resonance imaging apparatus 100B according to the third embodiment.

[Constituents of the Magnetic Resonance Imaging Apparatus 100B]

As compared with the magnetic resonance imaging apparatus 100A according to the second embodiment shown in FIG. 5, the magnetic resonance imaging apparatus 100A according the third embodiment shown in FIG. 7 further comprises a notification function 173. Further, in the present embodiment, the description of the constituent elements that are identical to the magnetic resonance imaging apparatus 100A is omitted.

In this embodiment, the fourth processing circuitry 17 further includes the notification function 173.

Depending on the operating conditions of the magnetic resonance imaging apparatus 100B, the notification function 173 notifies and prompts to the user.

For example, when the determination function 172 determines that the size of the region of interest is smaller than the lower limit of the predetermined range i.e. the prescribed size that can be supported by the local excitation scan (i.e., the size of the region of interest is smaller than the prescribed range), the notification function 173 may issue an alert on the display 12 to alert that a local excitation scanning can't be performed.

Further, it is also possible that, when the determination function 172 determines that the size of the region of interest is smaller than the lower limit of the prescribed range i.e. the prescribed size that can be supported by the local excitation scan (i.e., the size of the region of interest is smaller than the prescribed range), the notification function 173 may output a message to prompt that a local excitation scanning can't be performed. [Magnetic resonance imaging method performed by the magnetic resonance imaging apparatus 100B]

The magnetic resonance imaging method performed by the magnetic resonance imaging apparatus 100B will be described with reference to FIG. 8 and FIG. 9. Here, for steps that are identical to the steps in the flowchart shown in FIG. 3 and FIG. 6, the same reference numerals are assigned and the detailed description thereof will be omitted.

As shown in FIG. 8, after the magnetic resonance imaging apparatus 100B of the present embodiment starts to work, the actions of steps S200-S208 are performed identically to the magnetic resonance imaging apparatus 100 of the first embodiment, and after the action of step S208 ends, it is proceeded to step S500.

Next, in step S500, the size of the region of interest ROI adjusted in step S208 is determined by the determination function 172 whether it is less than a predetermined size.

When the determination function 172 determines that the size of the region of interest ROI is not less than the predetermined size (NO in step S502), in the next step S504, the second scan function 152 performs a non-local excitation scan to obtain the data, and then the process ends.

On the other hand, when the determination function 172 determines that the size of the region of interest ROI is smaller than the predetermined size (YES in step S500), it is proceeded to step S502.

Next, in step S502, the determination function 172 further determines whether the size of the region of interest ROI adjusted in step S208 is smaller than the prescribed size (i.e. whether the size of the region of interest is smaller than the prescribed range). Here, the prescribed size is a lower limit of a prescribed range that a local excitation scan can be performed, i.e., when the size of the ROI is smaller than the prescribed size (i.e., size of the region of interest is smaller than the prescribed range), a local excitation scan can't be performed. Depending on differences of the scanned objects, the prescribed sizes may be of different values.

When the determination function 172 determines that the size of the region of interest ROI is not less than the prescribed size (NO in step S502), in the next step S504, the second scan function 152 performs a non-local excitation scan by the local excitation scan function 1521 to obtain the data, and then the process ends.

On the other hand, when the determination function 172 determines that the size of the region of interest ROI is smaller than the prescribed size (i.e., size of the region of interest is smaller than the prescribed range) (YES in step S500), it is proceeded to step S700.

In step S700, an alert is issued on the display 12 to alert the user that it is beyond the range that can be supported by a local excitation scan, and a local excitation scan can't be performed and the process ends thereafter. In the following, the magnetic resonance imaging method performed by the magnetic resonance imaging apparatus 100B will be described in connection with FIG. 9.

After the magnetic resonance imaging apparatus 100B performs the processing of steps S200 to S208 identically to that of the magnetic resonance imaging apparatus 100 of the first embodiment 100, FIGS. 9(a) to (f) are obtained. Wherein FIGS. 9(a) to (c) are the locator images (FIG. 9(a), (b)) and the reference images (FIG. 9(c)) before adjustment by the adjustment function 171, and FIGS. 9(d) to (f) are the locator images (FIG. 9(e), (f)) and the reference images (FIG. 9(d)) after the adjustment by the adjustment function 171.

In the following step S500, when the determination function 172 determines that the size of the region of interest ROI is smaller than the predetermined size (YES in step S500), the determination function 172 further determines whether the size of the region of interest ROI is smaller than the range that can be supported by the local excitation scan (e.g. determines whether it is smaller than the prescribed size). In this example display, it is determined that the size of the region of interest ROI is smaller than the prescribed size, i.e. the size of the region of interest is smaller than the prescribed range (YES in step S700), the process proceeds to step S700, and in step S700, as shown in FIG. 9(d), an alert is issued by displaying a warning symbol to alert the user that is beyond the range that can be supported by a local excitation scan, and a local excitation scan can't be performed.

By the magnetic resonance imaging apparatus 100B of the third embodiment, in addition to having the effects of the first embodiment and the second embodiment, since it is also determined whether the size of the region of interest is beyond (smaller than) the range that can be supported by a local scan excitation, it avoids the user to adjust the size of the region of interest too small to result in a case where the subsequent local excitation scan can't be performed, and thereby avoids inducing discomfort to the user, improves the comfort of use of magnetic resonance imaging apparatus.

Variation Example 1 of the Third Embodiment

In the above-described third embodiment, when the size of the region of interest after adjustment is less than a prescribed range that can be supported by the local excitation scan, an alert is issued to alert the user that it exceeds the range that can be supported by a local excitation scan, but this is not a limit, and like the variation example 1, it is also possible that, when the size of the region of interest after adjustment is less than the prescribed range that can be supported by the local excitation scan, a message can be output to notify the user that it exceeds the range that can be supported by the local excitation scan.

Further, the determination can also be performed in the adjustment process, when the size of the region of interest has been reduced to the prescribed size, the user is prompted so that he will not further reduce the size of the region of interest, or it is automatically set that the size of the region of interest can't be further reduced.

The magnetic resonance imaging apparatus of the variation example 1 also has the above described technical effects of the magnetic resonance imaging apparatus of the third embodiment.

Variation Example 2 of the Third Embodiment

In the present variation example 2, when the size of the region of interest after adjustment is less than a prescribed range that can be supported by the local excitation scan, a message is output to notify the user that it exceeds the range that can be supported by a local excitation scan, and the adjustment function 171 further automatically adjusts the size of the region of interest, so that it become a size that is within the prescribed range that can be supported by the local excitation scan, such that a local excitation scan can be performed.

The magnetic resonance imaging apparatus of the variation example 2 of the third embodiment, in addition to having the above described technical effects of the magnetic resonance imaging apparatus of the third embodiment, when the size of the region of interest after adjustment is less than a prescribed range that can be supported by the local excitation scan, it not only prompts the user, but also automatically makes the size of the region of interest become a size within the prescribed range. Thereby, without increasing the user's operation, it is possible to ensure the smooth work of the magnetic resonance imaging apparatus, avoid the situation that a local excitation scan can't be performed and there will be problems with the imaging of the magnetic resonance imaging.

Fourth Embodiment

In the above described embodiments, description is made taking the example of setting a linear region of interest (the region represented by the white solid line in FIGS. 4(a) and (b)) indicating a planar slice area on the locator image, but the embodiments are not limited thereto. For example, when a slice area or a volume area with a certain thickness is to be imaged, a region of interest set on the locator image may have a thickness. Hereinafter, this example will be described as a fourth embodiment.

Description in the fourth embodiment is also applicable to all of the first to third embodiments described above. Therefore, in the following, the constituent elements that have the same functions as the constituent elements described in each of the embodiments described above are assigned with the same reference numerals, and detailed description of the functions that are already described will be omitted.

FIG. 10 is a schematic view of an example display of a magnetic resonance imaging apparatus according to the fourth embodiment. For example, as illustrated in FIGS. 10(a) and (b), the locator image generation function 161 generates a locator image in the sagittal plane and a locator image in the coronal plane of a brain of the same subject similarly to the example illustrated in FIGS. 4(a) and (b), and displays each of the generated locater images on the display 12.

Then, in the present embodiment, the interface 11 sets a region of interest with a thickness on the locator images displayed on the display 12 according to the operation of the operator. After the region of interest is set, the region of interest is displayed with a rectangular graphic on the locator images as indicated by an elongated rectangle represented by a black solid line in FIGS. 10(a) and (b) for example.

Further, in the present embodiment, the reference image generation function 162 generates a reference image including information on a thickness direction of the region of interest set by the interface 11 based on the 3D data obtained by the first scan function 151, and displays the reference image on the display 12. At this time, for example, the reference image generation function 162 generates, as the reference image, an image including information on a thickness direction (for example, thickness-added maximum intensity projection (MIP) or the like) by obtaining an average value, a maximum value, or a minimum value of pixel values at multiple sampling points along the thickness direction of the region of interest. In the example illustrated in FIG. 10, (c) illustrates the reference image.

Then, in the present embodiment, when the thickness of the region of interest on one of the locator image and the reference image is changed, the adjustment function 171 makes adjustments to correspondingly change the thickness of the region of interest on the other one of the locator image and the reference image. Here, (d) and (e) in FIG. 10 illustrate a state obtained after the region of interest is changed on the locator images illustrated in (a) and (b), and (f) illustrates a state obtained after the reference image illustrated in (c) is changed.

For example, as illustrated in FIGS. 10(d) and (e), when the interface 11 makes changes to increase the thickness of the region of interest set on the locator images, the adjustment function 171 causes the reference image generation function 162 to generate a reference image including information on a thickness direction corresponding to the changed thickness. Accordingly, the reference image with the increased information on the thickness direction is generated. Then, as illustrated in FIG. 10(f) for example, the adjustment function 171 displays the newly generated reference image on the display 12 in place of the reference image that has been displayed.

In contrast, as illustrated in FIGS. 10(a) and (b) for example, even when the interface 11 makes changes to reduce the thickness of the region of interest set in the locator images, the adjustment function 171 causes the reference image generation function 162 to generate a reference image including information on a thickness direction corresponding to the changed thickness. Accordingly, the reference image with the reduced information on the thickness direction is generated. Then, as illustrated in FIG. 10(c) for example, the adjustment function 171 displays the newly generated reference image on the display 12 in place of the reference image that has been displayed.

Meanwhile, for example, the adjustment function 171 receives a command to change the thickness of the region of interest on the reference image from the operator through operation of sliding, to the left and right, an arrow cursor for changing the thickness on the lower left side in FIGS. 10(c) and (f). Specifically, in the example illustrated in FIG. 10, the thickness of the region of interest is reduced when the cursor is moved to the left, and the thickness of the region of interest is increased when the cursor is moved to the right.

Then, as illustrated in FIG. 10(f) for example, when the cursor for changing the thickness is moved to the right, the adjustment function 171 causes the reference image generation function 162 to generate a reference image for which the information on the thickness direction is increased in accordance with the amount of movement of the cursor, and displays the reference image on the display 12. Further, in conjunction with this operation, the adjustment function 171 increases the thickness of the region of interest set on the locator images such that the thickness corresponds to the changed thickness as illustrated in FIGS. 10(d) and (e).

In contrast, as illustrated in FIG. 10(c) for example, when the cursor for changing the thickness is moved to the left, the adjustment function 171 causes the reference image generation function 162 to generate a reference image for which the information on the thickness direction is reduced in accordance with the amount of movement of the cursor, and displays the reference image on the display 12. Further, in conjunction with this operation, the adjustment function 171 reduces the thickness of the region of interest set on the locator image such that the thickness corresponds to the changed thickness as illustrated in FIGS. 10(a) and (b).

In this manner, by the magnetic resonance imaging apparatus of the fourth embodiment, display is made such that the thickness of the region of interest set on the locator image and the thickness of the reference image are changed in conjunction with each other. Therefore, the operator can intuitively and precisely set the thickness of the slice area or the volume area to be imaged while viewing the region of interest displayed on the locator image and the reference image.

Fifth Embodiment

In the above described embodiments, description is made taking the example of displaying the region of interest on the locator image, but the embodiments are not limited thereto. For example, in imaging by the magnetic resonance imaging apparatus, over-sampling for collecting data in a wider range than the region of interest may be performed in order to prevent wrap artifacts (also referred to as aliasing). The wrap artifacts are artifacts that occur when a structure located outside the field of view appears in an image. When the over-sampling is performed to prevent wrap artifacts, an over-sampling region (also referred to as a no-wrap region), which is set as a target range for the over-sampling, may be additionally displayed on the locator image. Hereinafter, this example will be described as a fifth embodiment.

Description in the fifth embodiment is also applicable to all of the first to fourth embodiments described above. Therefore, in the following, the constituent elements that have the same functions as the constituent elements described in each of the embodiments described above are assigned with the same reference numerals, and detailed description of the functions that are already described will be omitted.

FIG. 11 is a schematic view of an example display of a magnetic resonance imaging apparatus according to the fifth embodiment. For example, as illustrated in FIG. 11(a), the locator image generation function 161 generates a locator image in the coronal plane of a brain of a subject similarly to the example illustrated in FIG. 4, and displays the locator image on the display 12.

Then, in the present embodiment, the interface 11 sets an over-sampling region on the locator image displayed on the display 12 according to the operation of the operator. For example, the over-sampling region may be set in advance as one of the imaging conditions in accordance with a site to be imaged, an imaging purpose, or the like. After the over-sampling region is set, the over-sampling region is displayed with a rectangular graphic on the locator image as indicated by an elongated rectangle represented by a black dashed line in FIG. 11(a) for example. At this time, as indicated by an elongated rectangle represented by a black solid line in FIG. 11(a) for example, the region of interest is also displayed with a rectangular graphic on the locator image similarly to the embodiment as described above.

Further, in the present embodiment, as illustrated in FIG. 11(b) for example, the reference image generation function 162 generates a reference image including the region of interest set on the locator image and a peripheral region of the region of interest based on the 3D data obtained by the first scan function 151, and displays the reference image on the display 12. Accordingly, a range including the region of interest set on the locator image and the peripheral region of the region of interest is displayed in a display region of the reference image on the display 12.

At this time, for example, the reference image generation function 162 detects a body surface of the subject from the 3D data by performing image processing, such as background masking, and generates a reference image including a region that is obtained by adding a predetermined margin to a range including the detected body surface. Alternatively, for example, the reference image generation function 162 may generate a reference image including a region that is twice the size of the region of interest or a region with a size that is obtained by adding a predetermined margin to the twice the size of the region of interest. Alternatively, for example, the reference image generation function 162 may generate a reference image including a region with the same size as the over-sampling region that is set in advance as one of the imaging conditions or a region with a size that is obtained by adding a predetermined margin to the size of the over-sampling region.

Furthermore, in the present embodiment, the adjustment function 171 displays the over-sampling region for performing over-sampling to prevent wrap artifacts in a range including the region of interest set on the locator image and the peripheral region of the region of interest. For example, the adjustment function 171 displays the over-sampling region with a rectangular graphic as indicated by an elongated rectangle represented by a black dashed line in FIG. 11(b). Moreover, the adjustment function 171 displays the region of interest with a rectangular graphic as indicated by an elongated rectangle represented by a black solid line in FIG. 11(b) for example.

Then, in the present embodiment, when the size or position of the over-sampling region on one of the locator image and the reference image is changed, the adjustment function 171 makes adjustments to correspondingly change the size or position of the over-sampling region on the other one of the locator image and the reference image. Here, (c) in FIG. 11 illustrates a state obtained after the over-sampling region is changed on the locator image illustrated in (a), and (d) illustrates a state obtained after the over-sampling region is changed on the reference image illustrated in (b).

For example, as illustrated in FIG. 11(c), when the interface 11 makes changes to reduce the size of the over-sampling region set on the locator image, the adjustment function 171 changes the size of the over-sampling region displayed on the reference image so as to correspond to the changed size. Accordingly, as illustrated in FIG. 11(d) for example, the size of the over-sampling region displayed on the reference image is reduced as compared to the size that has been displayed.

In contrast, as illustrated in FIG. 11(a) for example, even when the interface 11 makes changes to increase the size of the over-sampling region set on the locator image, the adjustment function 171 changes the size of the over-sampling region displayed on the reference image so as to correspond to the changed size. Accordingly, as illustrated in FIG. 11(b) for example, the size of the over-sampling region displayed on the reference image is increased as compared to the size that has been displayed.

Alternatively, as illustrated in FIG. 11(d) for example, when the interface 11 makes changes to reduce the size of the over-sampling region set on the reference image, the adjustment function 171 changes the size of the over-sampling region displayed on the locator image so as to correspond to the changed size. Accordingly, as illustrated in FIG. 11(c) for example, the size of the over-sampling region displayed on the locator image is reduced as compared to the size that has been displayed.

In contrast, as illustrated in FIG. 11(a) for example, even when the interface 11 makes changes to increase the size of the over-sampling region set on the reference image, the adjustment function 171 changes the size of the over-sampling region displayed on the locator image so as to correspond to the changed size. Accordingly, as illustrated in FIG. 11(a) for example, the size of the over-sampling region displayed on the locator image is increased as compared to the size that has been displayed.

In this manner, by the magnetic resonance imaging apparatus of the fifth embodiment, display is made such that the size of the over-sampling region set on the locator image and the size of the over-sampling region displayed on the reference image are changed in conjunction with each other. Therefore, the operator can intuitively and precisely set the size of the over-sampling region while viewing the over-sampling region displayed on each of the locator image and the reference image.

FIG. 12 is a schematic view of another example display of the magnetic resonance imaging apparatus according to the fifth embodiment. FIG. 12 illustrates an example in which a leg of a subject is to be imaged, where (a) and (b) illustrate locator images of the coronal plane of the leg, and (c) illustrates a reference image of the leg corresponding to a region of interest set on the locator images. Further, an upper part in FIG. 12(c) indicates the head side in the head-to-foot direction of the subject, and a lower part indicates the foot side in the head-to-foot direction of the subject. Furthermore, (a) in FIG. 12 is a locator image corresponding to a position A indicated in the reference image in (c), and (b) is a locator image corresponding to a position B indicated in the reference image in (c).

For example, as indicated by rectangles represented by black solid lines in FIG. 12(a) to (c), when one of the two legs of the subject is to be imaged, a region of interest is set so as to include only the one leg to be imaged. Then, in this case, the over-sampling region is set so as to include the region of interest and a peripheral region of the region of interest as indicated by rectangles represented by black dashed lines in FIG. 12(a) to (c) to prevent occurrence of wrap artifacts due to the leg that is not to be imaged.

Here, as illustrated in FIG. 12(c) for example, the gap between the legs of the subject is normally reduced toward the crotch for the anatomical reason. Therefore, for example, the gap between the legs drawn on the locator image of a position close to the foot side as illustrated in FIG. 12(a) may be wider than the gap drawn on the locator image of a position close to the head side as illustrated in FIG. 12(b).

In this case, when only the locator image of the position close to the foot side is viewed, and if the size of the over-sampling region is excessively increased, the leg that is not to be imaged may be included more than expected in the over-sampling region on the side close to the head side, and, as a result, it may become difficult to appropriately remove wrap artifacts.

In the present embodiment, even in the situations as described above, the operator can easily recognize the positional relationship between the leg that is not to be imaged and the over-sampling region by using the reference image; therefore, it becomes possible to appropriately set the size of the over-sampling region.

In the first to third embodiments, when zoom-out operation or zoom-in operation is performed on the reference image, the adjustment function 171 changes the display magnification without changing the display size of the reference image; however, in the present embodiment, for example, it may be possible to change the display size of the reference image without changing the display magnification of the reference image. Alternatively, for example, the adjustment function 171 may display the reference image by small-screen embedded display using a display method, such as a picture-in-picture (PinP) or wipe. This makes it possible to ensure a display range with a size capable of displaying the over-sampling region on the reference image.

Variation Example

In the above described embodiments, the detailed description is made taking the example of the situations that the specific form of the present invention is magnetic resonance imaging apparatus and the method it performs, but the specific form of the present invention is not limited thereto, and it can also take various form of magnetic resonance imaging systems, methods, integrated circuits etc.

Further, in the description of the above embodiments, a case where the magnetic resonance imaging apparatus includes a first scan function 151 and a second scan function 152 are described, but it is not limited thereto, but may also be provided with only one scan function, the one scan function can perform the functions of the first scan function 151, the second scan function 152 and even the local excitation scan function 1521 and the non-local excitation scan function 1522.

Further, in the variation examples 1 and 2 of the third embodiment, issuing a message can be displaying a text message, making various messages such as a sound message or voice message etc.

Further, in the above embodiments, detailed description is made to the example of the object of the magnetic resonance imaging as the brain of human, but is not limited thereto, the object can be also small joints, pituitary, stomach, ligaments, elbow, wrist joints, ankle joints and other human organs.

Further, in the above described embodiments, with respect to the adjusting performed by the adjustment function 171, description is made taking the example of dragging a cursor displayed on the display 12, but the adjustment method may also be various adjustment methods of click, double click, pan, rotate, slide, multi-touch and move, stretch, shortening etc.

Further, in the above described embodiments, description is made taking the example in which both of the locator image generation function 161 and the reference image generation function 162 generate images based on the 3D data obtained by the first scan function 151, but the embodiments are not limited thereto. That is, the 3D data used by the locator image generation function 161 and the reference image generation function 162 may be the same data or different data. For example, when the reference image generation function 162 generates the reference image, if 3D data that is more appropriate to generate the reference image is already collected in addition to the 3D data that was used to generate the locator image, the reference image generation function 162 may generate the reference image based on the appropriate 3D data.

Each of the processing functions, provided by each of the processing circuitries, is explained above. Here, for example, each of the above-described processing functions is stored in the memory circuitry 13 in the form of program executable by a computer. Each of the processing circuitries reads each program from the memory circuitry 13 and executes each read program so as to implement the processing function that corresponds to each program. In other words, in a state where each program has been read, each of the processing circuitries has each of the processing functions that are illustrated in FIG. 2, FIG. 5 and FIG. 7. Furthermore, each processing function, provided by each of the processing circuitries, may be implemented by being separated or integrated into one or more processing circuitries as appropriate.

The term of the "processer", used in the above explanation, means for example a central processing unit (CPU), a graphical processing unit (GPU), or a circuit, such as an application specific integrated circuit (ASIC) or a programmable logic device (e.g., a simple programmable logic device (SPLD), a complex programmable logic device (CPLD), or a field programmable gate array (FPGA)). Here, a configuration may be such that, instead of storing programs in the memory circuitry, a program is directly installed in a circuit of the processor. In this case, the processor reads and executes a program that is installed in the circuit to implement the function. Furthermore, each processor according to the present embodiment is not always configured as a single circuit for each processor, and multiple separate circuits may be combined to be configured as a single processor so as to perform the function.

According to at least one of the above-described embodiments, it is possible to provide an intuitive preview.

Although the present invention has been disclosed with reference to specific embodiments herein, it should be understood that all the embodiments and examples described above are merely illustrative of the present invention but are not to be construed as limiting the present invention. Various modifications, improvements or equivalents can be devised by those skilled in the art without departing from the spirit and scope of the invention, and such modifications, improvements or equivalents should be considered to fall within the scope of the present invention.

What is claimed is:

1. A magnetic resonance imaging apparatus, comprising:
a display configured to display at least a locator image and a reference image;
an input interface configured to set a region of interest on the locator image displayed on the display; and
processing circuitry configured to
obtain three dimensional data of a subject,
generate the locator image from the three dimensional data and display the locator image on the display,
generate the reference image corresponding to the location of the region of interest and display the reference image on the display,
when the reference image is zoomed in or zoomed out by the input interface, adjust the size of the region of interest being set on the locator image so as to correspond to an area of the reference image, the area being displayed by the display after the reference image has been zoomed in or zoomed out, and,
when the region of interest being set on the locator image is increased or reduced by the input interface, zoom in or zoom out the reference image so as to correspond to the region of interest having been increased or reduced.

2. The magnetic resonance imaging apparatus according to claim 1, wherein
the processing circuitry further scans a part of the subject corresponding to the region of interest to obtain image data.

3. The magnetic resonance imaging apparatus according to claim 1, wherein
the processing circuitry generates a multi-plane reconstruction (MPR) image at a predetermined position and orientation from the three dimensional data, as the locator image.

4. The magnetic resonance imaging apparatus according to claim 1, wherein
the processing circuitry generates a volumetric rendering image rendered from a predetermined orientation from the three dimensional data as the locator image.

5. The magnetic resonance imaging apparatus according to claim 2, wherein
the processing circuitry applies a local excitation scan to obtain two dimensional or three dimensional data of the part corresponding to the region of interest from the subject.

6. The magnetic resonance imaging apparatus according to claim 1, wherein
the processing circuitry obtains volumetric data as the three dimensional data.

7. The magnetic resonance imaging apparatus according to claim 1, wherein
the processing circuitry obtains a multi-slice image as the three dimensional data.

8. A magnetic resonance imaging apparatus, comprising:
a display configured to display at least a locator image and a reference image;
an input interface configured to set a region of interest on the locator image displayed on the display; and
processing circuitry configured to
obtain three dimensional data of a subject,
generate the locator image from the three dimensional data and display the locator image on the display,
generate the reference image corresponding to a location of the region of interest and display the reference image on the display,
make, when a size or position of one of the region of interest on the locator image and the reference image is changed by the input interface, adjustments to correspondingly change the display magnification or position of the other of the region of interest on the locator image and the reference image,
determine whether the size of the region of interest is smaller than a predetermined size, and
scan a part of the subject corresponding to the region of interest to obtain image data, wherein,
when determining that the size of the region of interest is within a prescribed range, the processing circuitry performs a local excitation scan, and, when determining that the size of the region of interest is greater than the prescribed range, the processing circuitry performs a non-local excitation scan.

9. The magnetic resonance imaging apparatus according to claim 8, wherein,
when determining that the size of the region of interest is smaller than the prescribed range supported by the local excitation scan, the processing circuitry further issues an alert on the display to alert that the local excitation scan cannot be performed.

10. The magnetic resonance imaging apparatus according to claim 8, wherein,
when determining that the size of the region of interest is smaller than the prescribed range supported by the local excitation scan, the processing circuitry further issues a message to indicate that the local excitation scan cannot be performed.

11. The magnetic resonance imaging apparatus according to claim 8, wherein,
when determining that the size of the region of interest is smaller than the prescribed range supported by the local excitation scan, the processing circuitry further issues a message to indicate that the local excitation scan cannot be performed, and
the processing circuitry automatically adjusts the size of the region of interest to turn it into the size within the prescribed range that can be supported.

12. A magnetic resonance imaging apparatus, comprising:
a display configured to display at least a locator image and a reference image;
an input interface configured to set a region of interest with a thickness on the locator image displayed on the display; and
processing circuitry configured to
obtain three dimensional data of a subject,
generate the locator image from the three dimensional data and display the locator image on the display,
generate the reference image corresponding to a location of the region of interest and including information on a thickness direction of the region of interest and display the reference image on the display, and
make, when the thickness of one of the region of interest on the locator image and the reference image is changed by the input interface, adjustments to correspondingly change the thickness of the other of the region of interest on the locator image and the reference image.

13. A magnetic resonance imaging apparatus, comprising:
a display configured to display at least a locator image and a reference image;
an input interface configured to set a region of interest on the locator image displayed on the display; and
processing circuitry configured to
obtain three dimensional data of a subject,
generate the locator image from the three dimensional data and display the locator image on the display,
generate the reference image corresponding to a location of the region of interest and including the region of interest and a peripheral region of the region of interest and display the reference image on the display,
display an over-sampling region for performing over-sampling to prevent wrap artifacts in a range including the region of interest and the peripheral region of the region of interest, and
make, when a size or position of one of the region of interest on the locator image and the reference image is changed by the input interface, adjustments to correspondingly change the display magnification or position of the other of the region of interest on the locator image and the reference image.

14. The magnetic resonance imaging apparatus according to claim 13, wherein
the input interface sets the over-sampling region on the locator image, and
the processing circuitry makes, when a size or position of the over-sampling region on one of the locator image and the reference image is changed, adjustments to correspondingly change the size or position of the over-sampling region on the other one of the locator image and the reference image.

* * * * *